(12) United States Patent
Shan et al.

(10) Patent No.: US 11,980,361 B2
(45) Date of Patent: May 14, 2024

(54) CLOSURE DRIVING MECHANISM AND MEDICAL STAPLER INCLUDING THE SAME

(71) Applicant: Touchstone International Medical Science Co., Ltd., Suzhou (CN)

(72) Inventors: Teng Shan, Suzhou (CN); Yuanyang Cao, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 282 days.

(21) Appl. No.: 17/634,783

(22) PCT Filed: Aug. 27, 2020

(86) PCT No.: PCT/CN2020/111792
§ 371 (c)(1),
(2) Date: Feb. 11, 2022

(87) PCT Pub. No.: WO2021/037154
PCT Pub. Date: Mar. 4, 2021

(65) Prior Publication Data
US 2022/0323068 A1     Oct. 13, 2022

(30) Foreign Application Priority Data

Aug. 29, 2019 (CN) .................. 201910806840.X
Aug. 29, 2019 (CN) .................. 201910807054.1
(Continued)

(51) Int. Cl.
*A61B 17/068* (2006.01)
*A61B 17/115* (2006.01)

(52) U.S. Cl.
CPC .......... *A61B 17/068* (2013.01); *A61B 17/115* (2013.01)

(58) Field of Classification Search
CPC .. A61B 17/115; A61B 17/068; A61B 18/1445
(Continued)

(56) References Cited

U.S. PATENT DOCUMENTS

| 5,339,723 | A | * | 8/1994 | Huitema | ................. | F15B 13/16 |
| | | | | | | 91/428 |
| 9,192,431 | B2 | * | 11/2015 | Woodruff | ........... | A61B 18/1445 |

(Continued)

FOREIGN PATENT DOCUMENTS

| CN | 102791204 A | 11/2012 |
| CN | 106175863 A | 12/2016 |

(Continued)

OTHER PUBLICATIONS

English Translation of International Search Report issued for International Patent Application No. PCT/CN2020/111792 dated Mar. 4, 2021 (2 pages).

(Continued)

*Primary Examiner* — Robert F Long
*Assistant Examiner* — Xavier A Madison
(74) *Attorney, Agent, or Firm* — Fox Rothschild LLP

(57) ABSTRACT

The present disclosure provides a closure driving mechanism and a medical stapler including the same. The closure driving mechanism includes a driving part and a cylinder body, the driving part is connected with a closure pulling sheet of the stapler, and a cavity provided with a one-way valve is formed inside the cylinder body. When the driving part moves toward a distal side of the stapler, a volume of the cavity is decreased, the one-way valve is closed, and the driving part drives the closure pulling sheet to move distally, so as to open a head assembly of the stapler. Since the driving part is subjected to a resistance of compressed air in the cavity, a movement speed of the driving part is decreased, and the head assembly is opened slowly to (Continued)

prevent a force of opening the head assembly being too large to damage surrounding tissues.

20 Claims, 31 Drawing Sheets

(30) Foreign Application Priority Data

Aug. 29, 2019 (CN) .......................... 201921424809.1
Aug. 29, 2019 (CN) .......................... 201921425089.0

(58) Field of Classification Search
USPC ........................................... 227/175.1–182.1
See application file for complete search history.

(56) References Cited

U.S. PATENT DOCUMENTS

| | | | |
|---|---|---|---|
| 2007/0125826 | A1 | 6/2007 | Shelton, IV |
| 2007/0194081 | A1 | 8/2007 | Hueil et al. |
| 2010/0264194 | A1 | 10/2010 | Huang et al. |
| 2015/0136833 | A1 | 5/2015 | Shelton, IV et al. |
| 2017/0296173 | A1 | 10/2017 | Shelton, IV et al. |

FOREIGN PATENT DOCUMENTS

| | | | |
|---|---|---|---|
| CN | 106821440 | A | 6/2017 |
| CN | 109310427 | A | 2/2019 |
| CN | 210990509 | U | 7/2020 |
| CN | 210990511 | U | 7/2020 |
| EP | 3123956 | A2 | 2/2017 |
| EP | 3235446 | A2 | 10/2017 |
| JP | H09164144 | A | 6/1997 |
| JP | 2007000634 | A | 1/2007 |
| JP | 2008212672 | A | 9/2008 |
| JP | 2011224375 | A | 11/2011 |
| JP | 2014531262 | A | 11/2014 |
| JP | 2018521789 | A | 8/2018 |
| RU | 2559019 | C2 | 8/2015 |

OTHER PUBLICATIONS

Office Action dated Aug. 31, 2022 for Russian Patent Application No. 2022106012/14(012560) (17 pages).
Japanese Notice of Reasons for Refusal dated Apr. 21, 2023 for Japanese Patent Application No. 2022-512732 (3 pages).
Extended European Search Report dated Aug. 7, 2023 for European Patent Application No. 20856653.9 (10 pages).

\* cited by examiner

CLOSURE DRIVING MECHANISM AND MEDICAL STAPLER INCLUDING THE SAME

CROSS-REFERENCE TO RELATED APPLICATIONS

This application is based upon PCT patent application No. PCT/CN2020/111792, filed on Aug. 27, 2020, which claims priority to Chinese Patent Applications No. 201910807054.1, No. 201921425089.0, No. 201910806840.X and No. 201921424809.1, filed on Aug. 29, 2019, the entire contents of which are incorporated herein by reference.

TECHNICAL FIELD

The present disclosure relates to the field of medical instrument technology, in particular to a closure driving mechanism and a medical stapler including the same.

BACKGROUND

Digestive tract disease is one of human diseases of high incidence. During treatment, a medical stapler is widely used for suturing physiological tissues such as tissues in the digestive tract, instead of the manual operation by doctors. The medical stapler is a common surgical instrument, and used for end-to-end anastomosis, or end-to-side anastomosis of the physiological tissues of esophagus, stomach, intestine, etc., in a way of axial internal stapling. During the process of anastomoses, two sections of tissues are accommodated in the medical stapler, and a circular anastomotic stoma is formed after firing the medical stapler, to rebuild a tissue channel.

In the prior art, the medical stapler includes an instrument body, an operating handle rotatably connected to the instrument body and a head assembly cooperated with the instrument body. The head assembly includes two jaws: a staple cartridge and a staple anvil arranged oppositely. During operation, pressing the operating handle for a first time, a closure pulling sheet will be pulled to move toward a proximal side of the stapler by a closure driving mechanism, to close the staple cartridge and the staple anvil; pressing the operating handle again, anastomosis staples in the staple cartridge can be pushed to move toward the tissues, to anastomose the tissues by the forming of the anastomosis staples at the staple anvil. After the stapler is fired, the head assembly needs to be opened to separate the staple cartridge and the staple anvil. However, in the existing stapler, after the stapler is fired, the staple cartridge and the staple anvil will be separated suddenly and quickly, and the suddenly opened jaws may damage other tissues.

In the present disclosure, positions of the "distal side" and the "proximal side" are defined relative to an operator, wherein the "proximal side" is a side closer to the operator, and the "distal side" is another side far from the operator and closer to a surgical position.

SUMMARY

In view of the problems in the prior art, a purpose of the present disclosure is to provide a closure driving mechanism and a medical stapler including the same, which enable a head assembly to be slowly opened after the stapler is fired through a one-way air damping structure.

Embodiments of the present disclosure provide a closure driving mechanism applied on a medical stapler, wherein the closure driving mechanism includes a driving part and a cylinder body, the driving part is connected with a closure pulling sheet of the stapler, and the driving part is located at a proximal side of the cylinder body, wherein a cavity is formed inside the cylinder body, and the cavity is provided with a one-way valve; when the driving part moves toward a proximal side of the stapler, a volume of the cavity is increased, the one-way valve is opened, and the driving part drives the closure pulling sheet to move proximally, so as to close a head assembly of the stapler; when the driving part moves toward a distal side of the stapler, the volume of the cavity is decreased, the one-way valve is closed, and the driving part drives the closure pulling sheet to move distally, so as to open the head assembly of the stapler.

In some embodiments, the cylinder body is a part of a housing of the stapler.

In some embodiments, the one-way valve is disposed on a distal side of the cylinder body.

In some embodiments, the cavity is further provided with an air hole communicated with air.

In some embodiments, the driving part is at least partially located inside the cylinder body, and an inner wall of the cylinder body and the driving part are enclosed to form the cavity.

In some embodiments, the driving part is movable in an axial direction of the stapler relative to the proximal side of the cylinder body.

In some embodiments, a first sealing member is provided between an outer wall of the driving part and the inner wall of the cylinder body.

In some embodiments, the driving part includes a first driving member and a second driving member, the first driving member is at least partially located inside the cylinder body, and the second driving member is connected between the first driving member and the closure pulling sheet.

In some embodiments, the closure driving mechanism further includes a sleeve tube, the cylinder body and the driving part are both sleeved on the sleeve tube, and the driving part is movable in an axial direction of the sleeve tube; wherein a second sealing member is provided between an outer wall of the sleeve tube and the cylinder body.

In some embodiments, an outer wall of the cylinder body is provided with at least one first fixing part, and the housing of the stapler is provided with a second fixing part matched with the first fixing part.

In some embodiments, the outer wall of the cylinder body is provided with at least one fixing slot, and the housing of the stapler is provided with a fixing beam matched with the fixing slot; or, the outer wall of the cylinder body is provided with at least one fixing beam, and the housing of the stapler is provided with a fixing slot matched with the fixing beam.

In some embodiments, the driving part is connected with the proximal side of the cylinder body, when the driving part moves in an axial direction of the stapler, the proximal side of the cylinder body is driven to move in the axial direction of the stapler, and a length of the cylinder body along the axial direction of the stapler is changed.

In some embodiments, the driving part comprises a first driving member and a second driving member, the first driving member is connected with the proximal side of the cylinder body, and the second driving member is connected between the first driving member and the closure pulling sheet.

In some embodiments, a side wall of the cylinder body is a flexible side wall, the flexible side wall of the cylinder body has an amount of bending deformation in an initial state, and when the driving part moves toward the proximal side of the stapler, the amount of the bending deformation of the flexible side wall is decreased.

In some embodiments, a side wall of the cylinder body is an elastic side wall, when the driving part drives the proximal side of the cylinder body to move toward the proximal side of the stapler, the elastic side wall of the cylinder body is pulled and elastically deformed.

In some embodiments, the cylinder body is a corrugated tube extending along the axial direction of the stapler, the corrugated tube has an amount of compressive deformation in the initial state, and when the driving part moves toward the proximal side of the stapler, the amount of the compressive deformation of the corrugated tube is decreased.

In some embodiments, the distal side of the cylinder body is fixed to the housing of the stapler.

In some embodiments, the closure driving mechanism further includes a biasing member and a pulling rope, wherein the biasing member and the pulling rope are connected with the driving part, respectively; when the head assembly of the stapler is driven to be closed, the pulling rope pulls the driving part to move toward the proximal side of the stapler, and the biasing member is deformed; when the head assembly of the stapler is driven to be opened, the driving part moves toward the distal side of the stapler under a restoring force of the biasing member.

In some embodiments, the biasing member is a compression spring disposed at a proximal side of the driving part.

In some embodiments, the closure driving mechanism further includes a movable handle, a slider and a turning support beam, the pulling rope is sleeved on the turning support beam, and two ends of the pulling rope are connected to the slider and the driving part, respectively; in the initial state, when the movable handle is pressed, the movable handle drives the slider to move toward the distal side of the stapler, and the slider pulls the driving part to move toward the proximal side of the stapler through the pulling rope.

In some embodiments, the closure driving mechanism further includes a locking member and an actuating rod, wherein the actuating rod includes a pressing portion, and initial positions of the slider and the pressing portion are located at a proximal side of the locking member; in the initial state, when the movable handle is pressed, the movable handle drives the actuating rod to move toward the distal side of the stapler, and the pressing portion of the actuating rod presses the locking member downward to be fitted with the slider; after the stapler being fired, the pressing portion of the actuating rod no longer presses the locking member, the locking member moves upward to be separated from the slider, and the driving part moves toward the distal end of the stapler under the restoring force of the biasing member.

The embodiments of the present disclosure further provide a medical stapler including the closure driving mechanism described above.

The closure driving mechanism and the medical stapler including the same provided by the present disclosure have the following advantages.

The closure driving mechanism applied on the medical stapler provided by the present disclosure includes a one-way air damping structure. When the head assembly is driven to be closed, the one-way valve is opened to communicate the cavity with outside air, and the head assembly will be closed when the driving part drives the closure pulling sheet to move toward the proximal side of the stapler. After the stapler is fired, the one-way valve is closed, the distal movement of the driving part compresses the air in the cavity, and the driving part will be slowed down by a resistance of the compressed air, so that the head assembly can be opened slowly to prevent a force of opening the jaws being too large to damage the surrounding tissues.

BRIEF DESCRIPTION OF THE DRAWINGS

By reading the detailed description of non-limiting embodiments with reference to the following drawings, other features, objects and advantages of the present disclosure will be more obvious.

DETAILED DESCRIPTION

Figure 1:
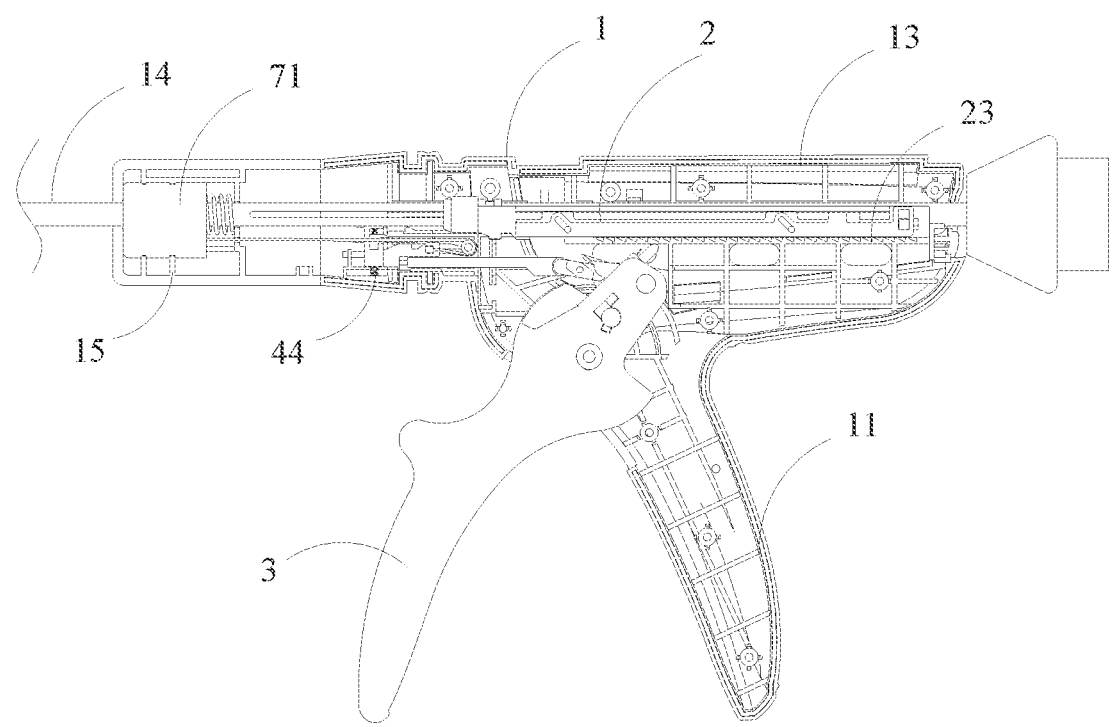
FIG. 1 is a partial schematic view of a stapler in an initial state according to a first embodiment of the present disclosure.

Example embodiments will now be fully described with reference to the accompanying drawings. However, the example embodiments can be implemented in various forms and should not be construed as limited to the embodiments described here; rather, these embodiments are provided to make the present disclosure comprehensive and complete, and to transmit the conception of the example embodiments comprehensively to those skilled in the art. The same reference symbols in the drawings indicate the same or similar structures, so their repeated descriptions will be omitted.

In order to solve the technical problems in the prior art, the present disclosure provides a closure driving mechanism applied on a medical stapler and the medical stapler including the same. The stapler includes a head assembly and an instrument body, and the instrument body is provided with a closure pulling sheet for closing the head assembly. The closure driving mechanism includes a driving part and a cylinder body, the driving part is connected with the closure pulling sheet and can pull the closure pulling sheet to move in an axial direction of the stapler.

A cavity is formed inside the cylinder body and the cavity is provided with a one-way valve, by which the driving part and the cylinder body together form an air damping structure. The one-way valve will be opened when subjected to a force in a first direction, making the cavity communicated with outside air, and the one-way valve will be closed when subjected to a force in a second direction, making the cavity become a closed cavity that is not communicated with the outside air.

Before firing the stapler, a staple cartridge and a staple anvil need to be closed by an operator to clamp the tissues. When the driving part moves toward a proximal side of the stapler, since a distance between a distal side wall of the driving part and a distal side wall of the cylinder body is increased, a volume of the cavity is increased, the one-way valve is opened by the force in the first direction, and the driving part drives the closure pulling sheet to move toward the proximal side of the stapler, thereby driving the head assembly to be closed. During this process, the one-way valve is opened to function as an air circulation channel, and as the proximal movement of the driving part, air will continuously enters the cavity to fill the increased space, so that the closing process of the head assembly will not be blocked.

After the stapler is fired, the driving part moves toward the distal side of the stapler. At this time, since the distance between the distal side wall of the driving part and the distal side wall of the cylinder body is decreased, the volume of the cavity is decreased, the one-way valve is closed by the force in the second direction, and the driving part drives the closure pulling sheet to move distally, thereby driving the head assembly of the stapler to be opened. In this process, the one-way valve is closed to make the cavity become a closed cavity, the air in the cavity is compressed as the volume of the cavity is decreased, and the movement speed of the driving part will be slowed down since the distal movement of the driving part is subjected to a resistance force from the compressed air, therefore, the head assembly of the stapler can be opened slowly to prevent the force of opening the jaws being too large to damage the surrounding tissues.

Structures of the closure driving mechanism and the stapler in the specific embodiments of the present disclosure will be further described below with reference to the accompanying drawings. Wherein, FIGS. 1 to 15 show multiple embodiments in which the driving part is axially movable relative to the proximal side of the cylinder body, and FIGS. 16 to 31 show multiple embodiments in which the driving part is fixedly connected with the proximal side of the cylinder body.

FIGS. 1 to 11 show the structure of the closure driving mechanism according to a first embodiment of the present disclosure. In the first embodiment, the driving part 61 is an integral part. FIGS. 12, 13, 14 and 15 show the structures of the closure driving mechanisms according to a second embodiment, a third embodiment, a fourth embodiment and a fifth embodiment of the present disclosure, respectively. In the four embodiments, the driving part includes two separately arranged components: a first driving member 611 and a second driving member 612.

FIGS. 1 to 7 show the structure of the closure driving mechanism in an initial state according to the first embodiment. The stapler includes an instrument body 1 and a head assembly (not shown in FIGS. 1 to 7) located on the distal side of the instrument body 1. The instrument body 1 includes a housing 13 and a fixed handle 11, further a closure pulling sheet 12 for closing and opening the head assembly is disposed inside the instrument body 1. When the closure pulling sheet 12 is in the initial state, the head assembly is opened; when the closure pulling sheet 12 moves toward the proximal side of the stapler, the head assembly is closed; and when the closure pulling sheet 12 moves toward the distal side of the stapler, the head assembly can be reopened.

As shown in FIGS. 1 to 4, the closure driving mechanism includes a driving part 61 and a cylinder body 71, the distal side of the driving part 61 is connected with the closure pulling sheet 12, and the driving part 61 can drive the closure pulling sheet 12 to move in the axial direction of the stapler. The driving part 61 is located at a proximal side of the cylinder body 71, and the driving part 61 is at least partially located inside the cylinder body 71. The inner wall of the cylinder body 71 and the driving part 61 are enclosed to form a cavity 74, and the cavity 74 is provided with a one-way valve 73. In this embodiment, the one-way valve 73 is disposed on a distal side of the cylinder body 71. When the one-way valve 73 is subjected to a force from the distal side to the proximal side of the stapler, the one-way valve 73 will be opened; and when the one-way valve 73 is subjected to a force from the proximal side to the distal side of the stapler, the one-way valve 73 will be closed. The driving part 61 can move in the axial direction of the stapler relative to the proximal side of the cylinder body 71 to change the volume of the cavity 74, therefore, the driving part 61 functions as a piston part cooperated with the cylinder body 71.

Figure 2:
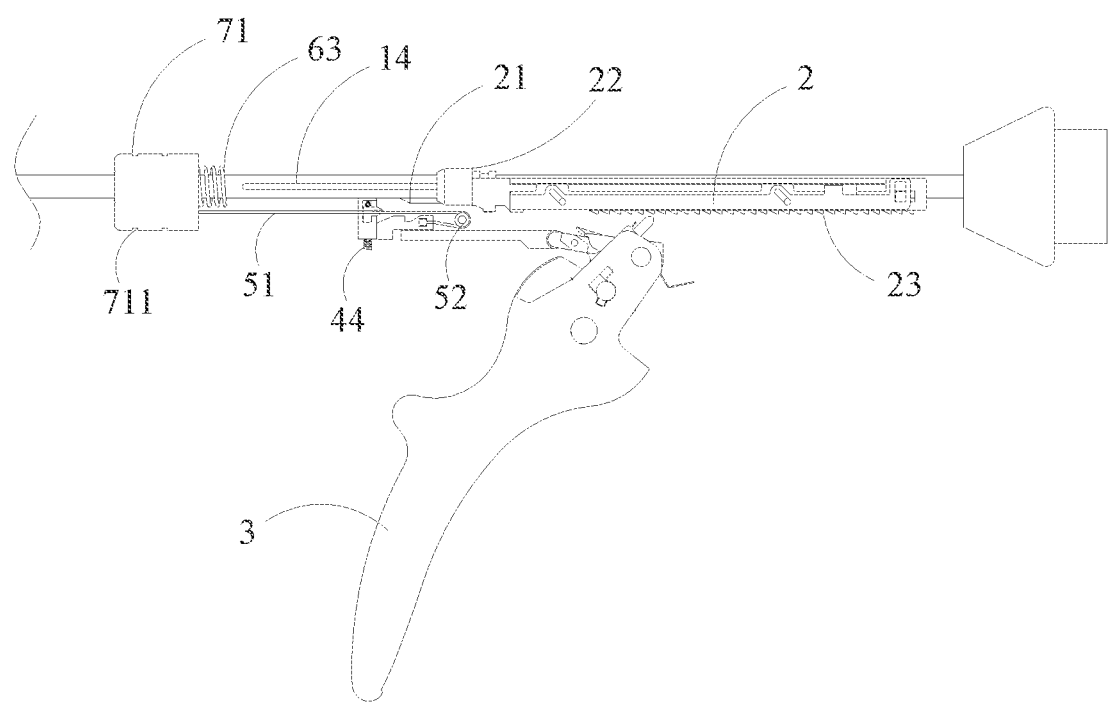
FIG. 2 is a schematic view of the stapler shown in FIG. 1 removing a housing.
Figure 5:
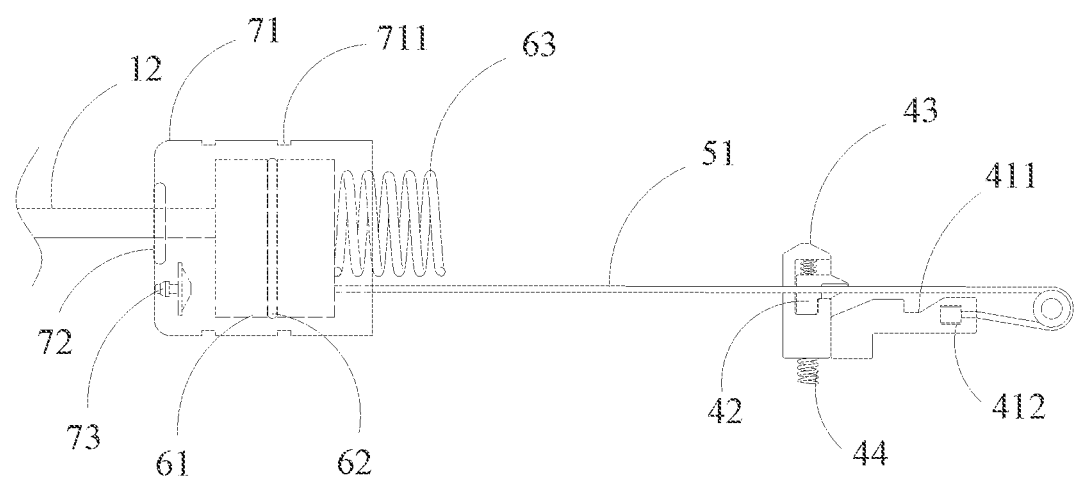
FIG. 5 is a schematic view of positional relation between the cylinder body and a driving part in the initial state according to the first embodiment of the present disclosure.

In the present disclosure, positions of the "distal side" and the "proximal side" are defined relative to the operator, wherein, the "distal side" is a side far from the operator, and the "proximal side" is another side closer to the operator. The term "distal movement" refers to a movement toward the distal side of the stapler, and the term "proximal movement" refers to a movement toward the proximal side of the stapler. The terms "distally" and "proximally" refer to "along a direction towards the distal side of the stapler" and "along a direction towards the proximal side of the stapler". The terms "upward" or "upward direction" is defined relative to an actuating rod 2, which refers to a direction faced toward a side away from a rack 23, and "downward" or "downward direction" refers to an opposite direction. For example, in the perspective of FIG. 1, the distal side of the instrument body 1 is the left side and the proximal side of the instrument body 1 is the right side. In the perspectives of FIGS. 1 and 2, the upward direction refers to a direction toward the upper end. As shown in FIG. 1 and FIG. 5, the closure driving mechanism further includes a sleeve tube 14, and the closure pulling sheet 12 is disposed inside the sleeve tube 14. The sleeve tube 14 extends along the axial direction of the stapler. Both the cylinder body 71 and the driving part 61 are sleeved outside of the sleeve tube 14. As shown in FIG. 1 and FIG. 2, in this embodiment, the outer wall of the cylinder body 71 is provided with at least one fixing slot 711, and the housing 13 of the stapler is provided with a fixing beam 15 matched with the fixing slot 711, thereby maintaining the position of the cylinder body 71 stable relative to the housing 13 during operation process of the stapler. In other alternative embodiments, the outer wall of the cylinder body 71 can be provided with at least one fixing beam and the housing 13 of the stapler is provided with a fixing slot matched with the fixing beam, so as to fix the cylinder body 71. In other alternative embodiments, the cylinder body 71 and the housing 13 can be relatively fixed by other fixing structures, such as bosses and grooves cooperated with each other. In addition, in other alternative embodiments, the cylinder body 71 can be movably disposed in the housing 13 of the stapler, instead of being fixed to the housing 13, or the cylinder body 71 can be fixed to the sleeve tube 14, etc., which all fall within the protection scope of the present disclosure. The cylinder body 71 may also be a part of the housing 13, that is, the cylinder body 71 and the housing 13 are integrally formed. In this embodiment, the housing 13 includes two parts, i.e., a first housing 13 and a second housing (not shown in the FIGS), correspondingly, the cylinder body 71 includes a first cylinder body disposed on the first housing 13 and a second cylinder body disposed on the second housing. When the first housing 13 and the second housing are fastened together, the first cylinder body and the second cylinder body are fastened to form the cylinder body 71.

Figure 3:
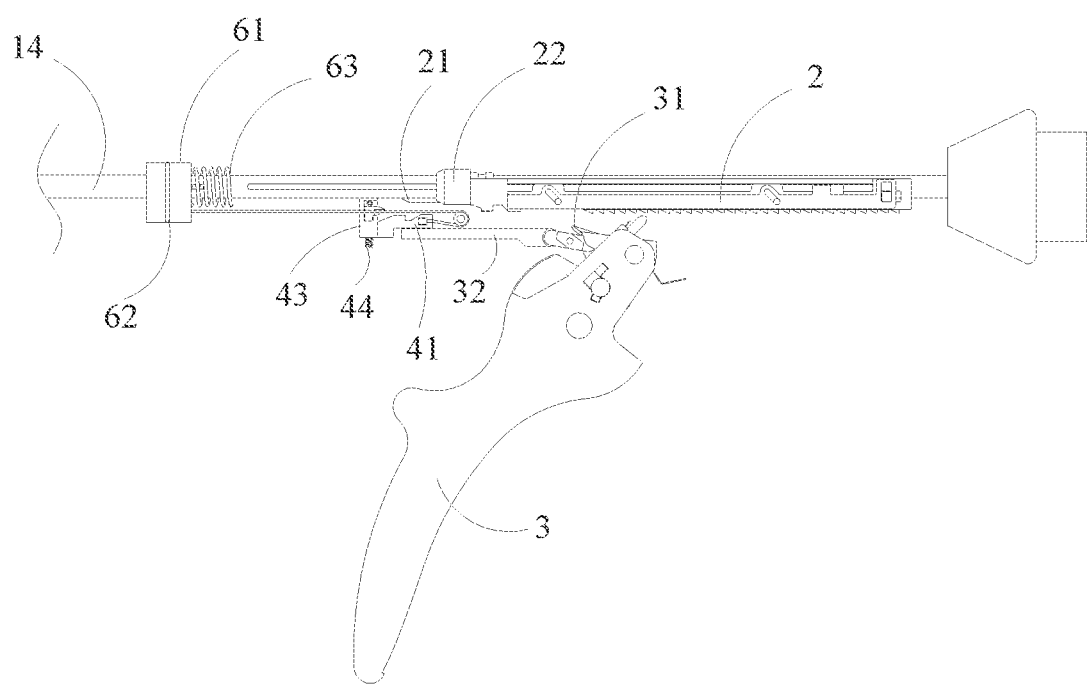
FIG. 3 is a schematic view of the stapler shown in FIG. 2 removing a cylinder body.
Figure 4:
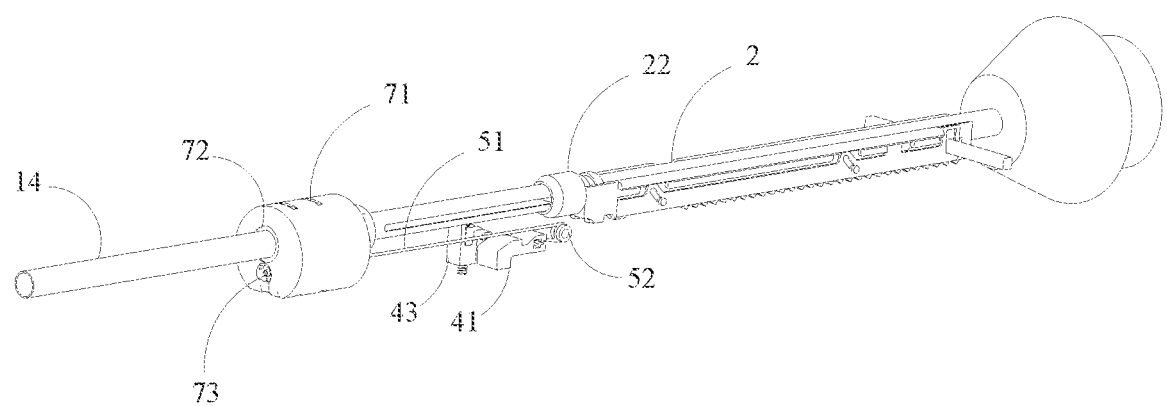
FIG. 4 is a schematic view of a closure driving mechanism in the initial state according to the first embodiment of the present disclosure.

As shown in FIG. 3, in order to achieve a better sealing effect between the outer wall of the driving part 61 and the inner wall of the cylinder body 71, preferably a first sealing member, specifically a first sealing ring 62 is provided between the outer wall of the driving part 61 and the inner wall of the cylinder body 71. The first sealing ring 62 can be made of flexible materials of rubber, plastic, etc. In other alternative embodiments of the present disclosure, instead of providing the first sealing ring 62, one of the driving part 61 and the cylinder body 71 can be made of flexible materials to achieve the sealing fit between the inner wall of the cylinder body 71 and the outer wall of the driving part 61. Providing the first sealing ring 62, or one of the driving part 61 and the cylinder body 71 being made of flexible materials can not only play the sealing role, but also increase the friction force during relative movement between the driving part 61 and the cylinder body 71, thereby making the opening and closing process of the jaws slow and stable.

As shown in FIG. 5, furthermore, in order to better achieve the airtight property of the cavity 74, the cylinder body 71 and the sleeve tube 14 are in a sealing fit, and preferably, a second sealing member, specifically a second sealing ring 72 is provided between the outer wall of the sleeve tube 14 and the inner wall of an opening where the cylinder body 71 is sleeved on the sleeve tube 14. The second sealing ring 72 can be made of flexible materials of rubber, plastic, etc.

Figure 6:
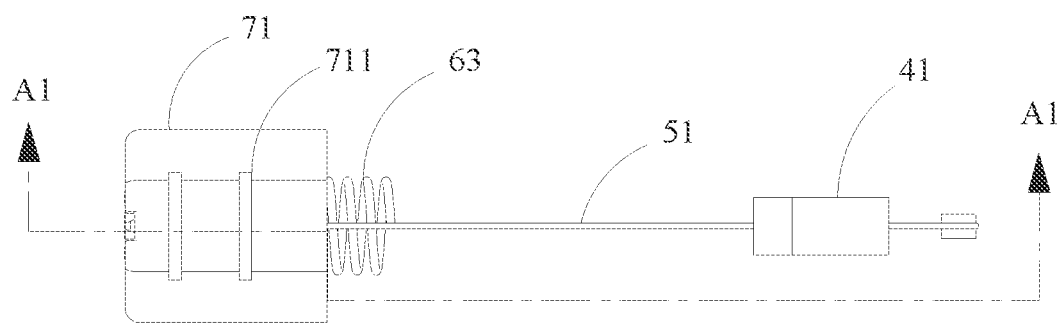
FIG. 6 is a top view of the closure driving mechanism in the initial state according to the first embodiment of the present disclosure.
Figure 7:
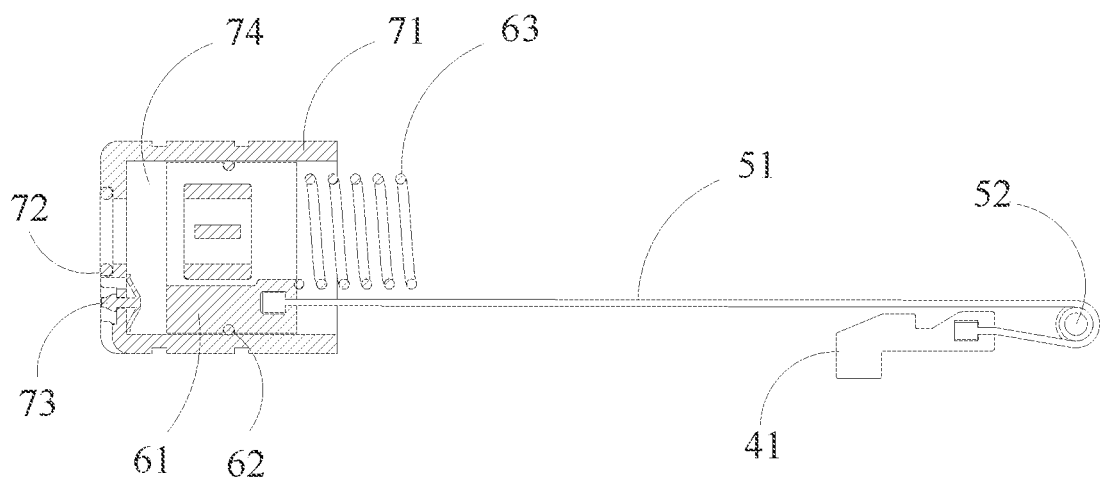
FIG. 7 is a sectional view in an A1-A1 direction shown in FIG. 6.

As shown in FIGS. 5 to 7, the closure driving mechanism further includes a movable handle 3, a biasing member, a pulling rope 51, a turning support beam 52 and a first slider 41. In order to reduce the resistance when the pulling rope 51 moves, the turning support beam 52 preferably uses a pulley structure. The biasing member applies a biasing force toward the distal side of the stapler on the driving part 61. In this embodiment, the biasing member is a first compression spring 63 disposed at a proximal side of the driving part 61. In other alternative embodiments, the biasing member may also use the structures like a tension spring, an elastic sheet, etc., which are not limited to those described here.

A side surface of the first slider 41 is provided with a second slot 412, one end of the pulling rope 51 is disposed in the second slot 412 and the other end of the pulling rope 51 is fixed to the driving part 61, thereby realizing a linkage between the first slider 41 and the driving part 61. In addition, after the movement of the first slider 41 is transmitted to the driving part 61 through the turning support beam 52, the moving direction of the first slider 41 is opposite to that of the driving part 61.

As shown in FIG. 5, the closure driving mechanism further includes a locking member and an actuating rod 2 extending along the axial direction of the stapler. The locking member includes a second slider 42 and a third slider 43, and a second compression spring 44 is disposed under the third slider 43. The actuating rod 2 includes a pressing portion 21 and a firing member 22. In the initial state, initial positions of the first slider 41 and the pressing portion 21 are both located at a proximal side of the locking member.

Figure 8:
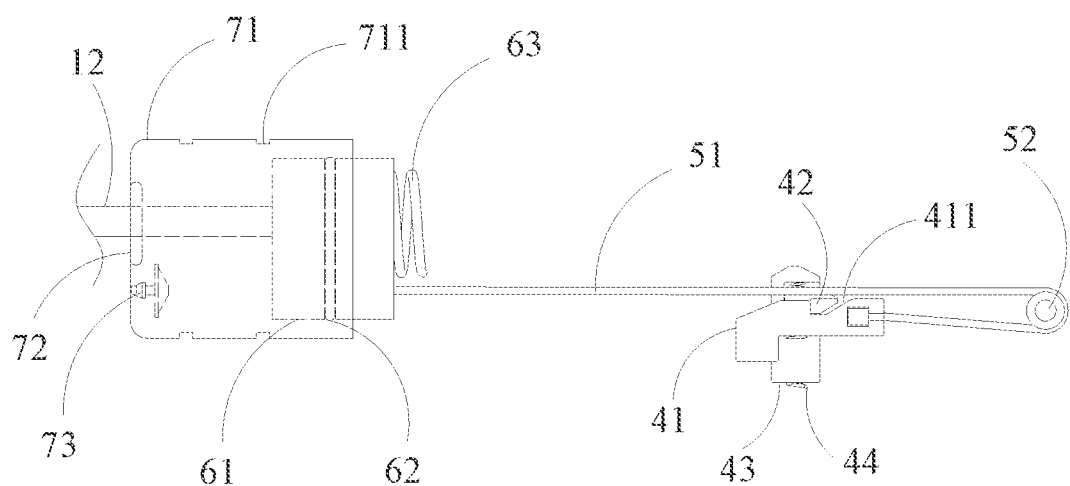
FIG. 8 is a schematic view of the positional relation between the cylinder body and the driving part during a firing process according to the first embodiment of the present disclosure.
Figure 9:
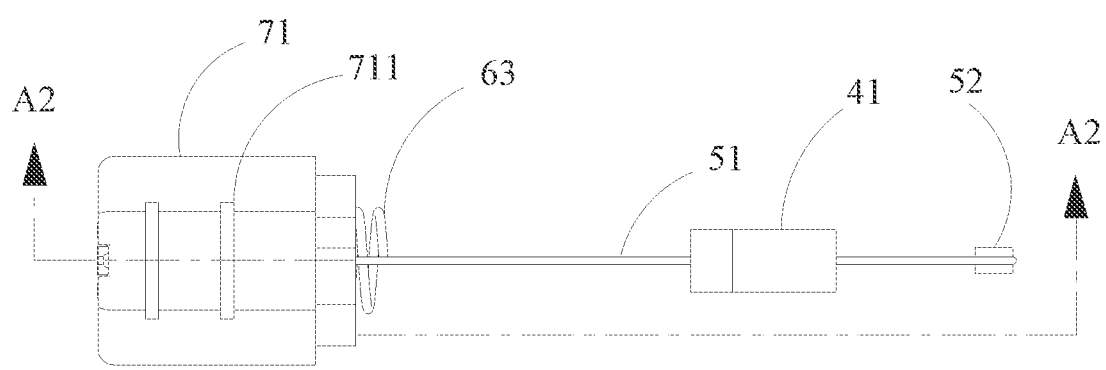
FIG. 9 is a top view of the closure driving mechanism during the firing process according to the first embodiment of the present disclosure.
Figure 10:
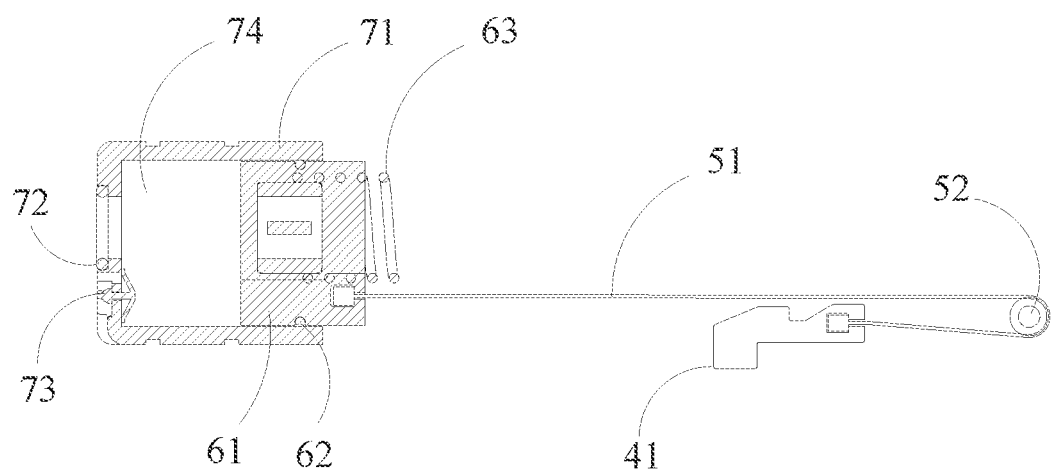
FIG. 10 is a sectional view in an A2-A2 direction shown in FIG. 9.

FIGS. 8 to 10 show the structure of the closure driving mechanism when the head assembly of the stapler is driven to be closed according to the first embodiment. In this embodiment, in the initial state, pressing the movable handle 3, the movable handle 3 will drive the first slider 41 to move toward the distal side of the stapler through the connecting rod 32, meanwhile, the movable handle 3 will drive the actuating rod 2 to move distally through a claw 31.

When the first slider 41 moves distally, the pulling rope 51 pulls the driving part 61 to move toward the proximal side of the stapler, and the driving part 61 compresses the first compression spring 63 to deform, meanwhile, the driving part 61 drives the closure pulling sheet 12 to move toward the proximal side of the stapler, so as to close the head assembly.

In the process of closing the head assembly, since the distance between the distal side wall of the driving part 61 and the distal side wall of the cylinder body 71 is gradually increased with the distal movement of the driving part 61, the volume of the cavity 74 enclosed by the driving part 61 and the cylinder body 71 is gradually increased, and the one-way valve 73 is opened by the force toward the proximal side of the stapler, forming the circulation channel between the cavity 74 and the outside air. Therefore, during the process of closing the head assembly, the one-way air damping structure will not block the movement of the driving part 61, and the head assembly can be normally closed to clamp the tissues.

As shown in FIG. 8, after the head assembly is closed, the first slider 41 moves under the locking member, meanwhile, the pressing portion 21 (not shown in FIG. 8) of the actuating rod 2 contacts an upper portion of the third slider 43 of the locking member and presses the third slider 43 downward, so that the second slider 42 of the locking member partially enters the first slot 411 on the upper surface of the first slider 41, to maintain the positional stability of the first slider 41 during the firing process of the stapler. At this time, the second compression spring 44 is compressively deformed by the second compression spring 44. During this process, the pulling force toward the proximal side of the stapler applied by the first slider 41 on the driving part 61 through the pulling rope 51 is equal to the restoring force of the first compression spring 63, therefore, the driving part 61 is maintained in the position shown in FIG. 10 under the pulling of the pulling rope 51, to maintain the closure stability of the head assembly during the firing process of the stapler.

Here, the cooperating manner of the first slider 41 and the locking member is only an embodiment. In other alternative embodiments, an upwardly concave groove can be disposed on a lower surface of the locking member, therefore, when the locking member is pressed downward by the pressing portion 21 of the actuating rod 2, the locking member will move downward, making the upper portion of the first slider 41 enter the groove of the locking member, and achieving a fitting between the locking member and the first slider 41.

Figure 11:
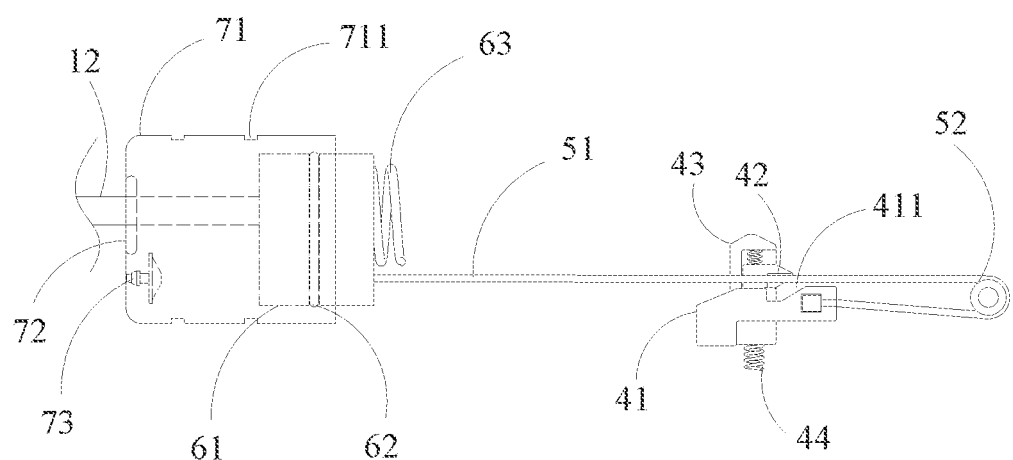
FIG. 11 is a schematic view of the positional relation between the cylinder body and the driving part after the firing is completed according to the first embodiment of the present disclosure.

FIG. 11 shows the structure of the closure driving mechanism after the stapler is fired in the first embodiment. At this time, the pressing portion 21 (shown in FIG. 3) of the actuating rod 2 no longer presses the third slider 43 downward, so the third slider 43 moves upward under the restoring force of the second compression spring 44, and drives the second slider 42 to move upward to be separated from the first slot 411 of the first slider 41. Losing the locking function of the locking member, the first slider 41 can move freely and no longer applies the pulling force toward the proximal side of the stapler on the driving part 61. There-fore, under the restoring force of the first compression spring 63, the driving part 61 moves toward the distal side of the stapler, and drives the closure pulling sheet 12 to move distally, so as to open the head assembly of the stapler.

During the opening process of the head assembly of the stapler, as the driving part 61 moves toward the distal side of the stapler, the distance between the distal side wall of the driving part 61 and the distal side wall of the cylinder body 71 is gradually decreased, the volume of the cavity 74 is gradually decreased, and the one-way valve 73 is closed by the force toward the distal side of the stapler. At this time, the cavity 74 is not communicated with the outside air, the air in the cavity 74 is gradually compressed as the volume of the cavity 74 is decreased, and the movement speed of the driving part 61 will be slowed down since the distal movement of the driving part 61 will be resisted by the compressed air, so that the head assembly of the stapler is opened slowly. In other alternative embodiments, the side wall of the cavity 74 may be provided with a small air hole communicated with outside air, the small air hole can only release air very slowly to the outside when the volume of the cavity 74 is decreased, and the release speed of the small air hole is not as fast as the speed at which the air is compressed, therefore the air still applies resistance on the distal movement of the driving part 61.

In addition, since the first sealing ring 62 is disposed between the outer wall of the driving part 61 and the inner wall of the cylinder body 71, the contact surface of the first sealing ring 62 and the cylinder body 71 further produces a certain damping for the distal movement of the driving part 61, which is also beneficial to slow down the movement speed of the driving part 61.

FIGS. 12 to 15 are schematic views of the closure driving mechanisms according to a second embodiment, a third embodiment, a fourth embodiment and a fifth embodiment of the present disclosure, respectively. Difference between the four embodiments and the first embodiment is that, the piston part 64 and the driving part 61 are separately disposed as two parts connected with each other. The piston part 64 is located at the proximal side of the cylinder body 71, and the size of the piston part 64 is matched with the size of the inner wall of the cylinder body 71 to form a sealing connection with the cylinder body 71. The shape and the size of the driving part 61 only need to be able to transmit the movement of the piston part 64 to the closure pulling sheet 12, and are not limited to the shape and the size shown in FIG. 14.

Figure 12:
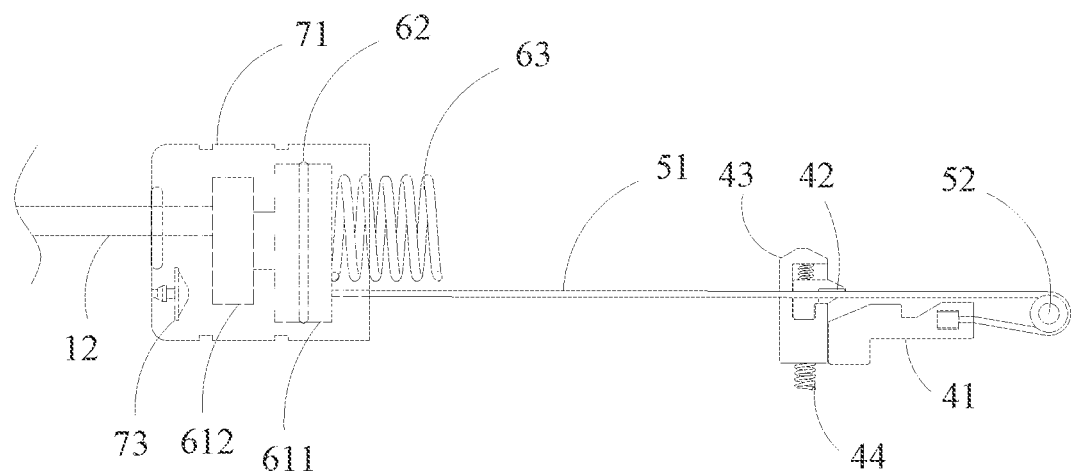
FIG. 12 is a schematic view of the closure driving mechanism in the initial state according to a second embodiment of the present disclosure.

As shown in FIG. 12, in the second embodiment, the driving part 61 includes a first driving member 611 and a second driving member 612. The first driving member 611 is at least partially located in the cavity of the cylinder body 71 to play the role of the piston part by cooperating with the inner wall of the cylinder body 71. The second driving member 612 is connected between the first driving member 611 and the closure pulling sheet 12, and the first driving member 611 is connected with the pulling rope 51. The size of the second driving member 612 may be smaller than that of the first driving member 611, so that the outer wall of the first driving member 611 and the inner wall of the cylinder body 71 form the sealing connection while the second driving member 612 and the cylinder body 71 do not form a sealing connection. Therefore, the movement of the second driving member 612 in the cavity will not affect the volume of the cavity, and only the movement of the first driving member 611 toward the distal side or the proximal side of the stapler will decrease or increase the volume of the cavity. The first driving member 611 can preferably be made of flexible materials or a first sealing ring 62 can be provided between the first driving member 611 and the inner wall of the cylinder body 71. Providing the first sealing ring 62 can not only play the sealing role, but also increase the friction force when the first driving member 611 and the cylinder body 71 move relatively, which makes the opening and closing process of the jaws slow and stable.

When the first driving member 611 moves to the proximal side of the stapler under the action of the pulling rope 51, since the distance between the distal side wall of the first driving member 611 and the distal side wall of the cylinder body 71 is increased, the volume of the cavity is increased, the one-way valve 73 is opened by the force toward the proximal side, and the first driving member 611 drives the second driving member 612 to move to the proximal side of the stapler, so as to drive the closure pulling sheet 12 of the stapler to move toward the proximal side of the stapler. Therefore, the head assembly of the stapler is driven to be closed, and at the same time, the first compression spring 63 at the proximal side is compressed and deformed by the first driving member 611. When the first driving member 611 moves to the distal side of the stapler under the action of the restoring force of the first compression spring 63, since the distance between the distal side wall of the first driving member 611 and the distal side wall of the cylinder body 71 is decreased, the volume of the cavity is decreased, the one-way valve 73 is closed by the force toward the distal side, the first driving member 611 drives the second driving element 612 to move toward the distal side of the stapler, and the second driving element 612 drives the closure pulling sheet 12 to move toward the distal side of the stapler, so as to drive the head assembly of the stapler to be opened. During this process, the air in the cavity is compressed as the volume of the cavity is decreased, so the movement speed of the piston part will be slowed down since the movement of the first driving member 611 to the distal side of the stapler will be resisted by the compressed air, making the head assembly of the stapler be opened slowly, and preventing the force of opening the jaws being too large to damage the surrounding tissues.

Figure 13:
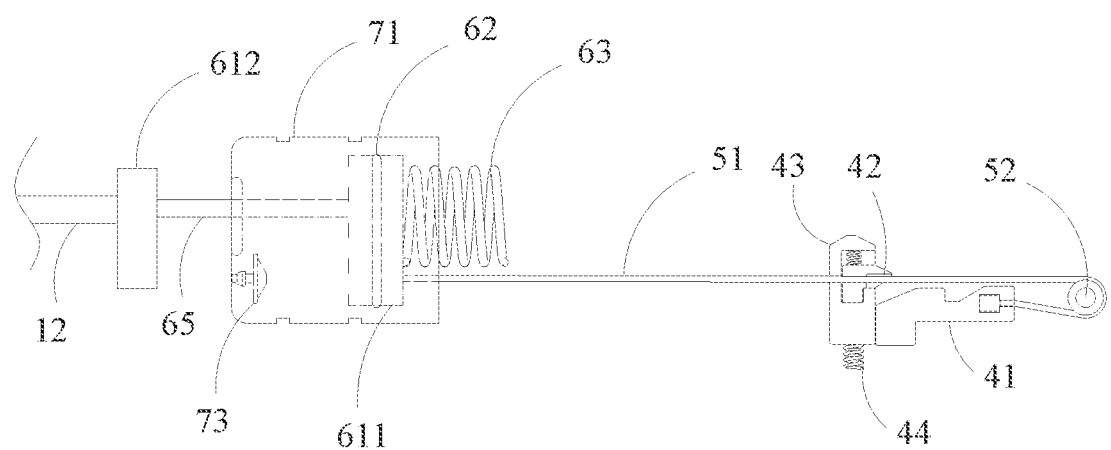
FIG. 13 is a schematic view of the closure driving mechanism in the initial state according to a third embodiment of the present disclosure.
Figure 14:
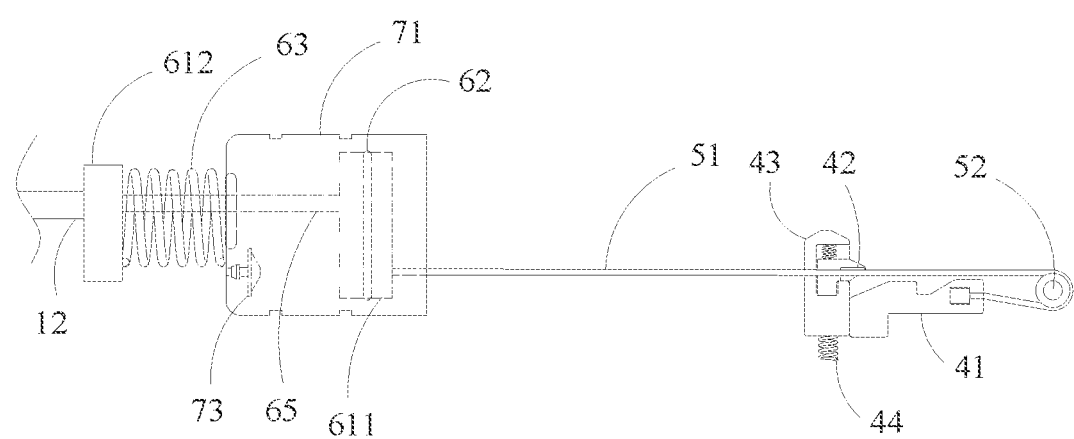
FIG. 14 is a schematic view of the closure driving mechanism in the initial state according to a fourth embodiment of the present disclosure.

As shown in FIG. 13, the difference of the third embodiment from the second embodiment is that, the second driving member 612 is located at the distal side of the cylinder body 71, and the second driving member 612 and the first driving member 611 are connected through a connecting rod 65. Since the second driving member 612 is outside the cylinder body 71, the movement of the second driving member 612 will not affect the volume of the cavity. As shown in FIG. 14, the difference of the fourth embodiment from the third embodiment is that, the first compression spring 63 is disposed between the proximal side of the second driving member 612 and the cylinder body 71 and can be sleeved on the connecting rod 65, rather than being disposed at the proximal side of the first driving member 611. Similarly, when the first driving member 611 moves toward the proximal side, a closure driving member 61 is pulled to move toward the proximal side, and the first compression spring 63 will be compressed and deformed by the closure driving member 61. After the pulling force applied on the first driving member 611 toward the proximal side from the pulling sheet 51 is released, the second driving member 612 moves distally under the restoring force of the first compression spring 63, and drives the closure pulling sheet 12 and the first driving member 611 to move distally.

Figure 15:
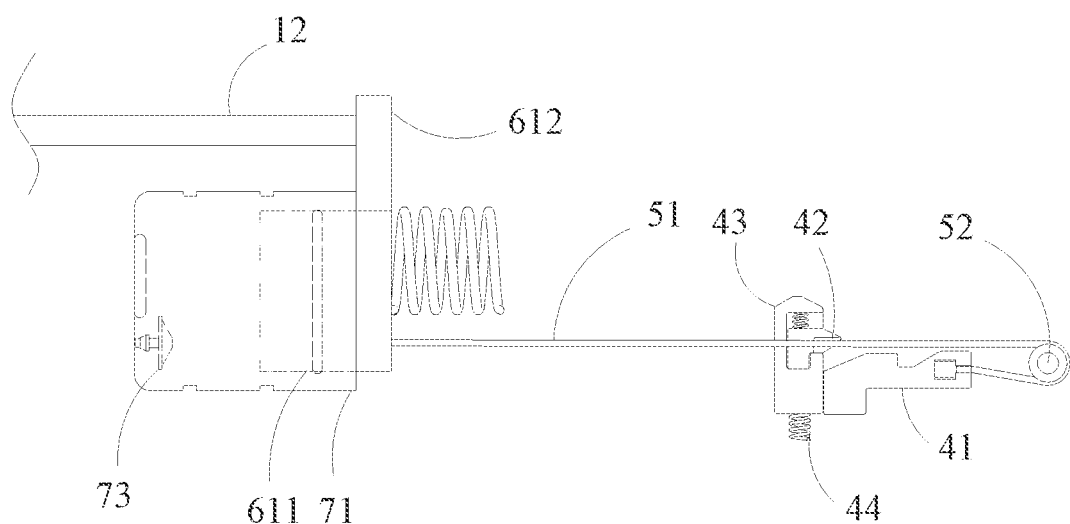
FIG. 15 is a schematic view of the closure driving mechanism in the initial state according to a fifth embodiment of the present disclosure.
Figure 16:
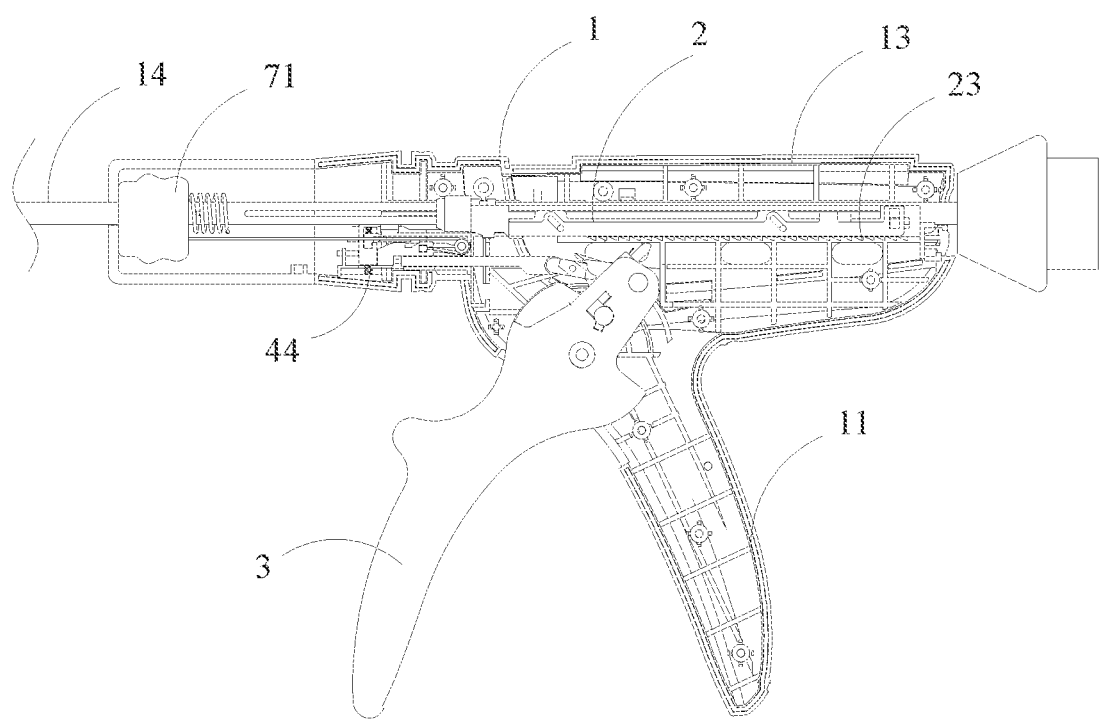
FIG. 16 is a schematic view of a cooperating structure of the closure driving mechanism and the housing of the stapler according to a sixth embodiment of the present disclosure.
Figure 17:
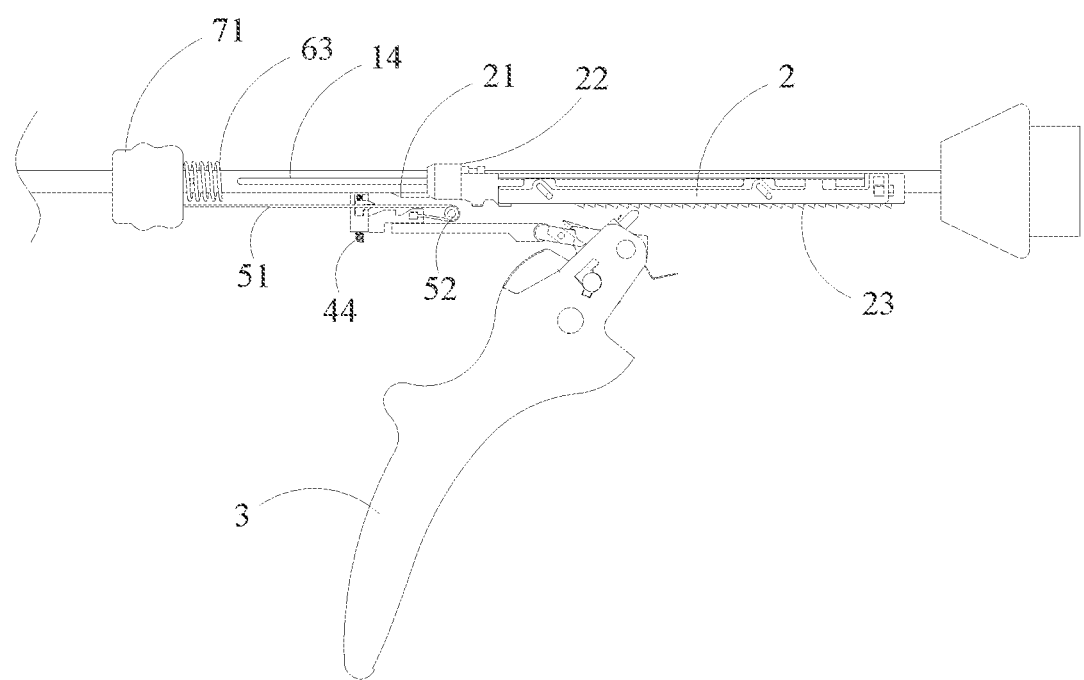
FIG. 17 is a schematic view of the stapler shown in FIG. 16 removing the housing.

FIG. 15 is a schematic view of the closure driving mechanism according to the fifth embodiment of the present disclosure. The difference of the fifth embodiment from the two embodiments shown in FIGS. 12 and 13 is that, the closure pulling sheet 12 and the first driving member 611 are not disposed coaxially, and the second driving member 612 can be fixedly connected to a side wall of the first driving member 611. In this embodiment, working principles of the second driving member 612 and the first driving member 611 are the same as those of the embodiment shown in FIG. 12 and FIG. 13, and will not be repeated here. On the basis of the fifth embodiment, at least two groups of the cylinder bodies 71 and the first driving members 611 can be provided, and the second driving member 612 is fixedly connected to a plurality of the first driving members 611 at the same time, and a plurality of the one-way valves 73 are disposed in the cavities 74 of the cylinder bodies 71, respectively.

In the embodiments shown in FIGS. 1 to 15, the cylinder body 71 is preferably made of materials that are not easily deformed, such as plastics, metals, etc. with high hardness, so as to ensure the stability of the structure and the position of the cylinder body 71. However, the present disclosure is not limited to those described here, in the embodiments shown in FIGS. 1 to 15, the cylinder body 71 may also have certain flexibility or elasticity, which all fall within the protection scope of the present disclosure.

In the following, embodiments using deformable cylinder bodies will be introduced further with reference to FIGS. 16 to 31. Wherein, the driving part is connected with the proximal side of the cylinder body and can drive the proximal side of the cylinder body to move in the axis direction of the stapler, and the volume of the cavity will be changed as a length of the side wall of the cylinder body is changed. Specifically, when the driving part moves toward the proximal side of the stapler, the closure pulling sheet and the proximal side of the cylinder body are driven to move toward the proximal side of the stapler, respectively, so the length of the cylinder body along the axial direction of the stapler is elongated, the volume of the cavity is increased, and the one-way valve is opened. When the driving part moves toward the distal side of the stapler, the closure pulling sheet and the proximal side of the cylinder body are driven to move toward the distal side of the stapler, therefore, the length of the cylinder body along the axial direction of the stapler is shortened, the volume of the cavity is decreased, and the one-way valve is closed.

FIGS. 16 to 21 show the structures of the closure driving mechanism and the stapler in the initial state according to a sixth embodiment. In this embodiment, the stapler includes an instrument body 1 and a head assembly (not shown in FIGS. 16 to 21) located on the distal side of the instrument body 1. The instrument body 1 includes a housing 13 and a fixed handle 11, further a sleeve tube 14 extending along the axial direction of the stapler is provided inside the instrument body 1, and a closure pulling sheet 12 for closing and opening the head assembly is disposed inside of the sleeve tube 14. When the closure pulling sheet 12 is in the initial state, the staple anvil and the staple cartridge are separated; when the closure pulling sheet 12 moves toward the proximal side of the stapler, the staple anvil and the staple cartridge are closed; and when the closure pulling sheet 12 moves toward the distal side of the stapler, the head assembly can be reopened.

As shown in FIGS. 16 to 19, the closure driving mechanism includes a driving part 61 and a cylinder body 71, and both the driving part 61 and the cylinder body 71 are sleeved outside the sleeve tube 14. The driving part 61 is connected with the closure pulling sheet 12 of the stapler to form a linkage between the driving part 61 and the closure pulling sheet 12. The driving part 61 is fixedly connected with the proximal side of the cylinder body 71 to form a linkage between the driving part 61 and the proximal side of the cylinder body 71. The cylinder body 71 is a deformable cylinder body, the distal side of which is fixed to the housing 1 of the stapler and the proximal side is axially movable with the driving part 61. A cavity 74 is formed inside the cylinder body 71, and the cavity 74 is provided with a one-way valve 73.

Figure 19:
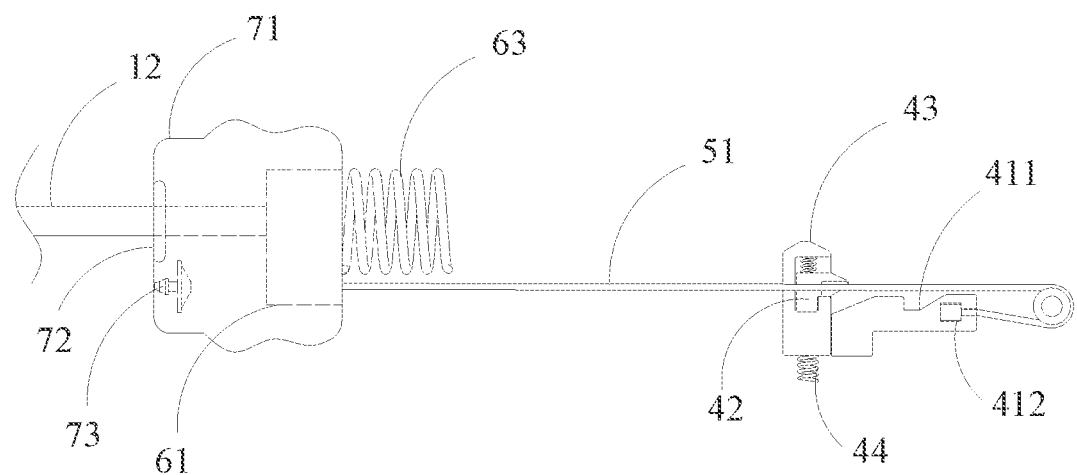
FIG. 19 is a schematic view of the closure driving mechanism in the initial state according to the sixth embodiment of the present disclosure.
Figure 20:
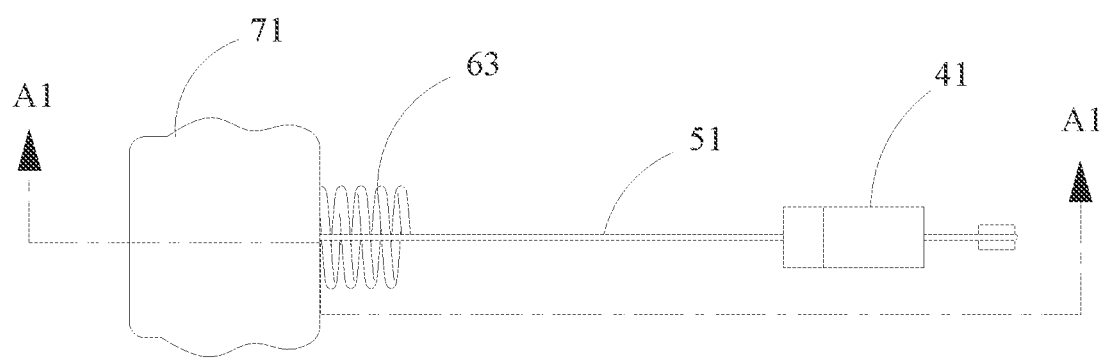
FIG. 20 is a top view of the closure driving mechanism in the initial state according to the sixth embodiment of the present disclosure.
Figure 21:
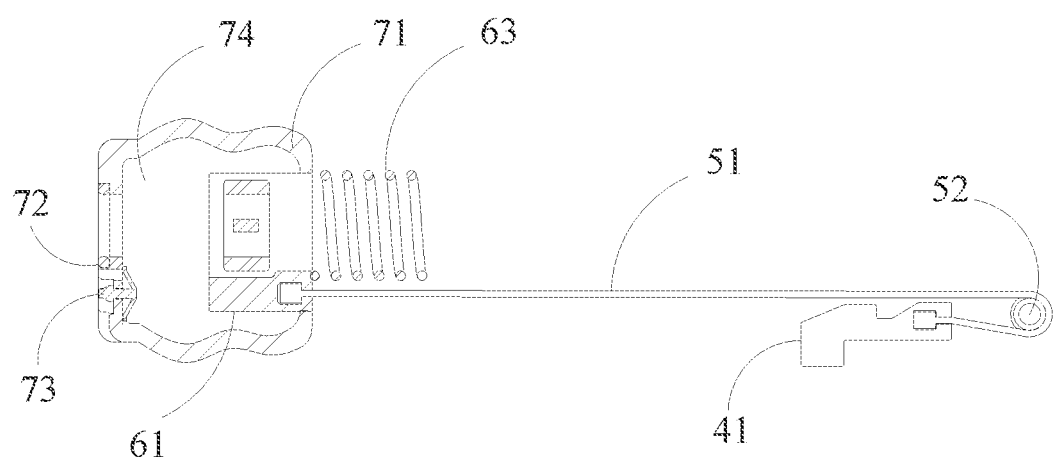
FIG. 21 is a sectional view in an A1-A1 direction shown in FIG. 20.

In this embodiment, the one-way valve 73 is disposed on the distal side of the cylinder body 71. When the one-way valve 73 is subjected to a force from the distal side to the proximal side of the stapler, the one-way valve 73 is opened, and the cavity 74 is communicated with outside air at this time. When the one-way valve 73 is subjected to a force from the proximal side to the distal side of the stapler, the one-way valve 73 is closed, and the cavity 74 forms a closed cavity at this time. As shown in FIGS. 19 to 21, in order to better achieve the airtight property of the cavity 74, the cylinder body 71 and the sleeve tube 14 are in a sealing connection, and a sealing member 72 is preferably disposed between the outer wall of the sleeve tube 14 and the inner wall of the opening where the cylinder body 71 is sleeved on the sleeve tube 14. The sealing member 72 can be a sealing ring, while the present disclosure is not limited to this, the sealing member 72 can be made of flexible materials of rubber, plastic, etc.

In this embodiment, the side wall of the cylinder body 71 is a flexible side wall, for example, the side wall is made of materials of plastic, textile material, etc. In a preferable embodiment, the distal side and the proximal side of the cylinder body 71 may be rigid, and only the side wall of the cylinder body 71 is deformable. In an alternative embodiment, entirety of the cylinder body 71 may be made of flexible materials of plastic, rubber, etc. As shown in FIG. 19 to FIG. 21, in the initial state, the flexible side wall of the cylinder body 71 has a predetermined amount of bending deformation.

In this embodiment, the distal side of the cylinder body 71 is fixed to the housing 13 of the stapler, to keep the position of the distal side of the cylinder body 71 relatively stable. When the proximal side of the cylinder body 71 moves in the axial direction of the stapler, the distance between the distal side of the cylinder body 71 and the proximal side of the cylinder body 71 changes accordingly.

As shown in FIGS. 18 to 21, the closure driving mechanism further includes a movable handle 3, a biasing member, a pulling rope 51, a turning support beam 52 and a first slider 41. In order to reduce the resistance when the pulling rope 51 moves, the turning support beam 52 preferably uses a pulley structure. The biasing member applies a biasing force toward the distal side of the stapler on the driving part 61. In this embodiment, the biasing member is a first compression spring 63 disposed at the proximal side of the driving part 61. In other alternative embodiments, the biasing member may be structures of a tension spring, an elastic sheet, etc., which are not limited to those described here.

A side surface of the first slider 41 is provided with a second slot 412, one end of the pulling rope 51 is disposed in the second slot 412 and the other end of the pulling rope 51 is fixed to the driving part 61, so as to realize the linkage between the first slider 41 and the driving part 61. In addition, after the movement of the first slider 41 is transmitted to the driving part 61 through the turning support beam 52, the moving direction of the first slider 41 is opposite to that of the driving part 61.

Figure 18:
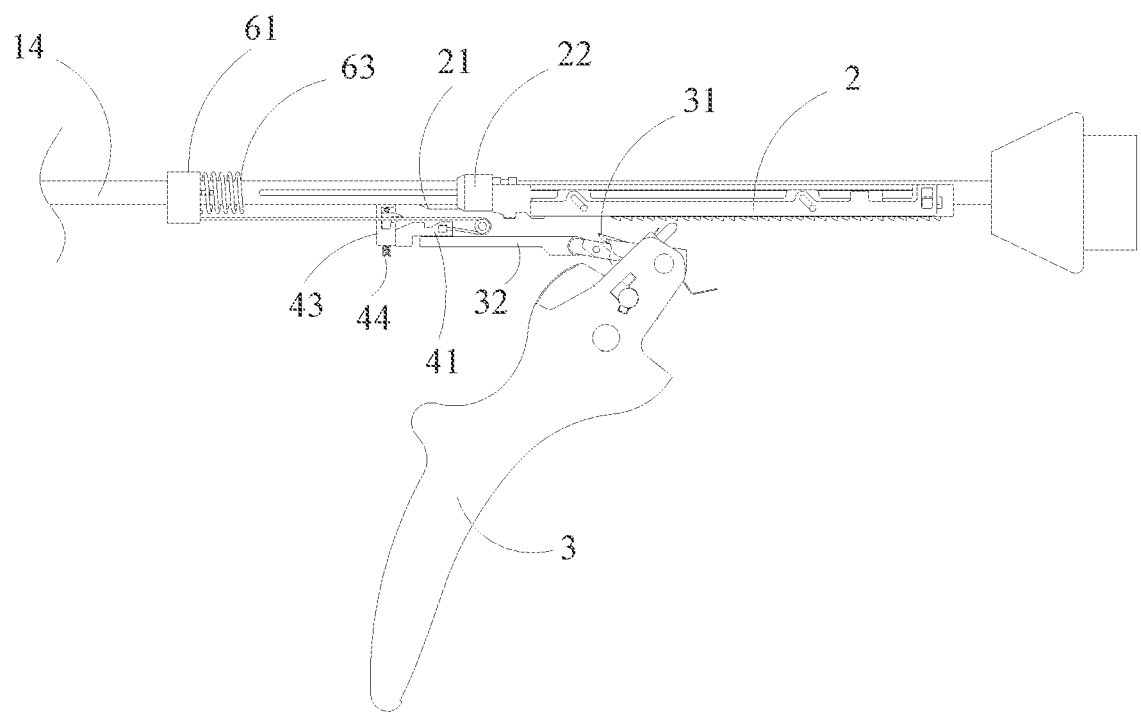
FIG. 18 is a structural view of the stapler shown in FIG. 17 removing the cylinder body.

As shown in FIG. 18, the closure driving mechanism further includes a locking member and an actuating rod 2 extending along the axial direction of the stapler. The locking member includes a second slider 42 and a third slider 43, and a second compression spring 44 is disposed under the third slider 43. The actuating rod 2 includes a pressing portion 21 and a firing member 22. In the initial state, initial positions of the first slider 41 and the pressing portion 21 are both located at the proximal side of the locking member.

Figure 22:
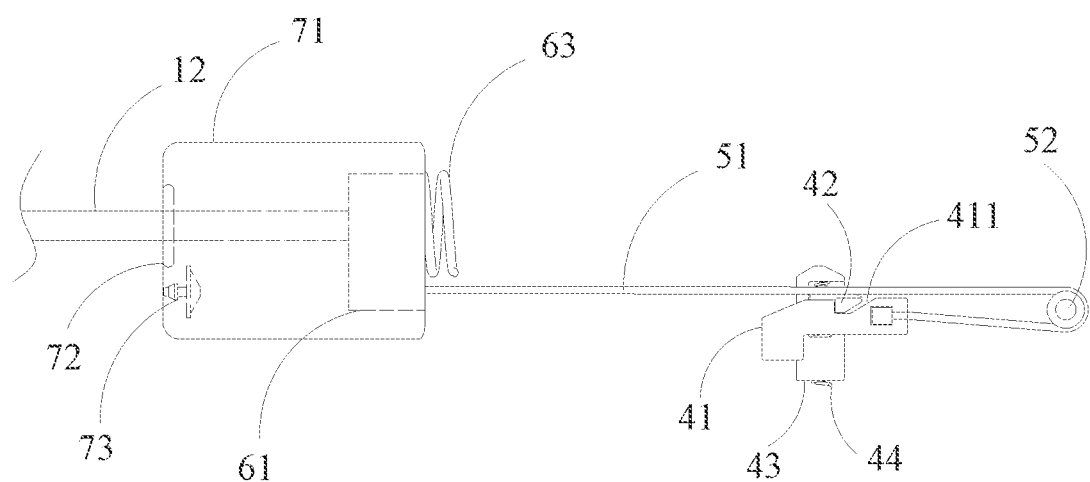
FIG. 22 is a schematic view of the closure driving mechanism after the head assembly is closed according to the sixth embodiment of the present disclosure.
Figure 23:
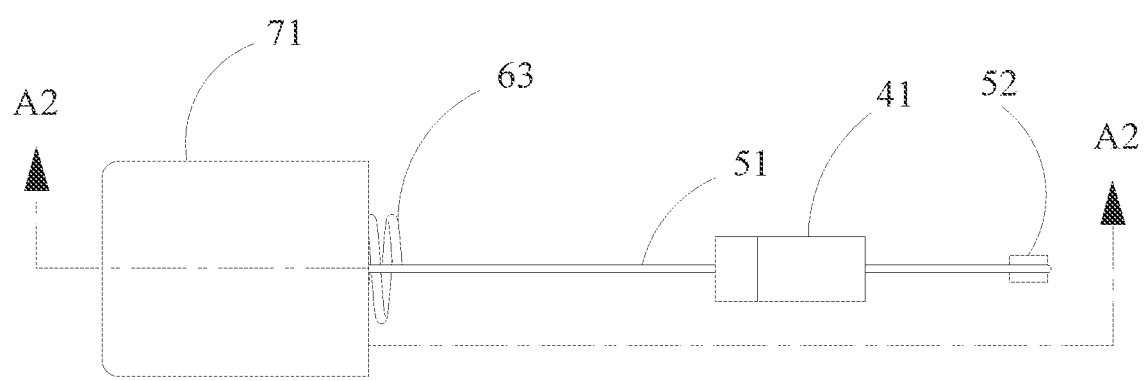
FIG. 23 is a top view of the closure driving mechanism after the head assembly is closed according to the sixth embodiment of the present disclosure.
Figure 24:
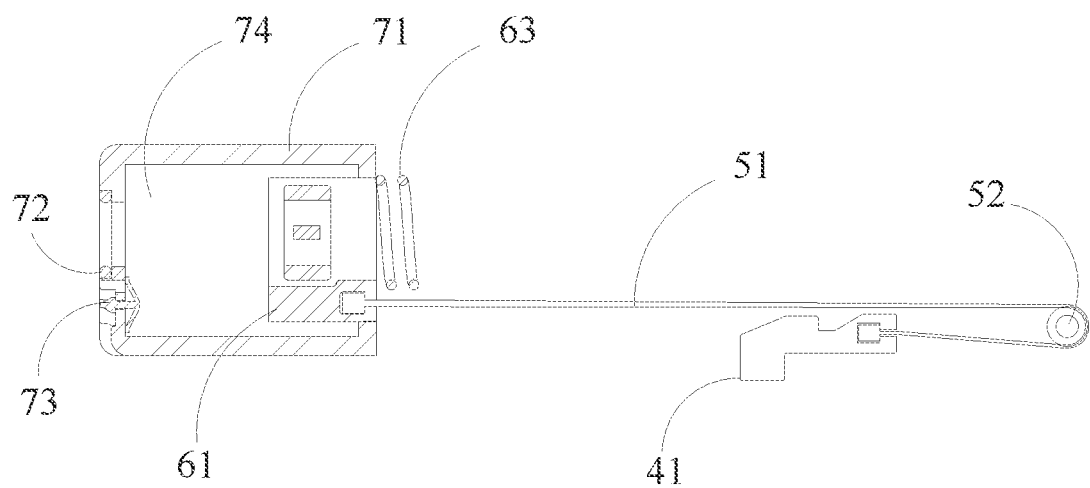
FIG. 24 is a sectional view in an A2-A2 direction shown in FIG. 23.

FIGS. 22 to 24 show the structure of the closure driving mechanism when the head assembly of the stapler is driven to be closed in the sixth embodiment. Pressing the movable handle 3, the movable handle 3 will drive the first slider 41 to move toward the distal side of the stapler through the connecting rod 32, and at the same time, the movable handle 3 will drive the actuating rod 2 to move distally through the claw 31. When the first slider 41 moves toward the distal side of the stapler, the driving part 61 is pulled by the pulling rope 51 to compress the first compression spring 63 to deform, the driving part 61 further drives the closure pulling sheet 12 to move toward the proximal side of the stapler, thereby driving the staple anvil and the staple cartridge to close the head assembly.

During the closing process of the head assembly, the driving part 61 further drives the proximal side of the cylinder body 71 to move proximally, the distance between the proximal side of the cylinder body 71 and the distal side of the cylinder body 71 is increased, the amount of the bending deformation of the cylinder body 71 is decreased, the length of the cylinder body 71 along the axial direction of the stapler is elongated, the volume of the cavity 74 is increased, and the one-way valve 73 is opened by the force toward the proximal side of the stapler, forming the circulation channel between the cavity 74 and the outside air. Therefore, in the closing process of the head assembly, the one-way air damping structure will not block the movement of the driving part 61, and the head assembly can be normally closed to clamp the tissues.

As shown in FIG. 22, when the head assembly is closed, the first slider 41 moves under the locking member, and at the same time, the pressing part 21 (shown in FIG. 17) of the actuating rod 2 contacts the upper portion of the third slider 43 of the locking member and presses the third slider 43 downward, so that the second slider 42 of the locking member partially enters the first slot 411 on the upper surface of the first slider 41, to keep the positional stability of the first slider 41 during the firing process of the stapler. At this time, the second compression spring 44 is compressed to deform by the third slider 43. During this process, since the pulling force toward the proximal side of the stapler applied by the first slider 41 on the driving part 61 through the pulling rope 51 is equal to the restoring force of the first compression spring 63, the driving part 61 is maintained in the position shown in FIG. 22 under the pulling of the pulling rope 51, thereby maintaining the closure stability of the head assembly during the firing process of the stapler.

Here, the cooperating manner of the first slider 41 and the locking member is only exemplarily. In other alternative embodiments, an upwardly concave groove can be disposed on the lower surface of the locking member, therefore, when the locking member is pressed downward by the pressing portion 21 of the actuating rod 2, the locking member moves downward, making the upper portion of the first slider 41 enter the groove of the locking member to achieve the snap fitting between the locking member and the first slider 41.

Figure 25:
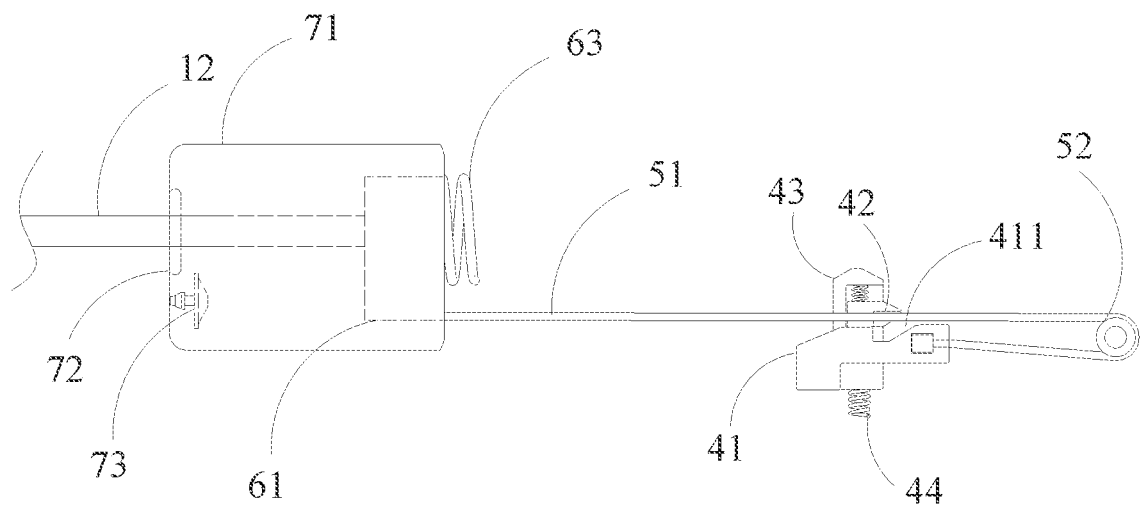
FIG. 25 is a schematic view of the closure driving mechanism after the stapler is fired according to the sixth embodiment of the present disclosure.

FIG. 25 shows the structure of the closure driving mechanism after the stapler is fired in the sixth embodiment. At this time, the pressing portion 21 (shown in FIG. 17) of the actuating rod 2 no longer presses the third slider 43 downward, so the third slider 43 moves upward under the restoring force of the second compression spring 44, and drives the second slider 42 to move upward to be separated from the first slot 411 of the first slider 41. Losing the holding function of the locking member, the first slider 41 can move freely and no longer applies the pulling force toward the proximal side of the stapler on the driving part 61. At this time, under the restoring force of the first compression spring 63, the driving part 61 moves toward the distal side of the stapler, drives the closure pulling sheet 12 to move distally, so as to drive the staple anvil and staple cartridge of the stapler to be separated to open the head assembly.

During the opening process of the head assembly of the stapler, as the driving part 61 moves toward the distal side of the stapler, the distance between the proximal side wall of the cylinder body 71 and the distal side wall of the cylinder body 71 is gradually decreased, the length of the cylinder body 71 along the axial direction of the stapler is gradually decreased, the volume of the cavity 74 is gradually decreased, and the one-way valve 73 is closed by the force toward the distal side of the stapler. At this time, the cavity 74 is not communicated with the outside air, the air in the cavity 74 is gradually compressed as the volume of the cavity 74 is decreased, and the movement speed of the driving part 61 will be slowed down since the distal movement of the driving part 61 will be resisted by the compressed air, so that the head assembly of the stapler can be opened slowly. In other alternative embodiments, further the side wall of the cavity 74 may be provided with a small air hole communicated with outside air, the small air hole can only release air very slowly to the outside when the volume of the cavity 74 is decreased, and the release speed of the small air hole is not as fast as the speed at which the air is compressed, therefore the air still produces resistance to the distal movement of the driving part 61. The opening of the small air hole is preferably smaller than the opening of the one-way valve 73 when the one-way valve 73 is opened, however, the present disclosure is not limited to those described here.

In an alternative embodiment, the side wall of the cylinder body 71 may be an elastic side wall which for example may be made of a rubber material that can produce tensile deformation and return to its original shape after the tensile deformation. In the initial state, the side wall of the cylinder body 71 is not deformed. When the driving part 61 drives the proximal side of the cylinder body 71 to move toward the proximal side of the stapler, the elastic side wall of the cylinder body 71 is pulled to produce elastic tensile deformation. When the driving part 61 drives the proximal side of the cylinder body 71 to move toward the distal side of the stapler, the elastic tensile deformation of the cylinder body 71 is gradually decreased, so that the length of the cylinder body 71 along the axial direction of the stapler is shortened.

Figure 26:
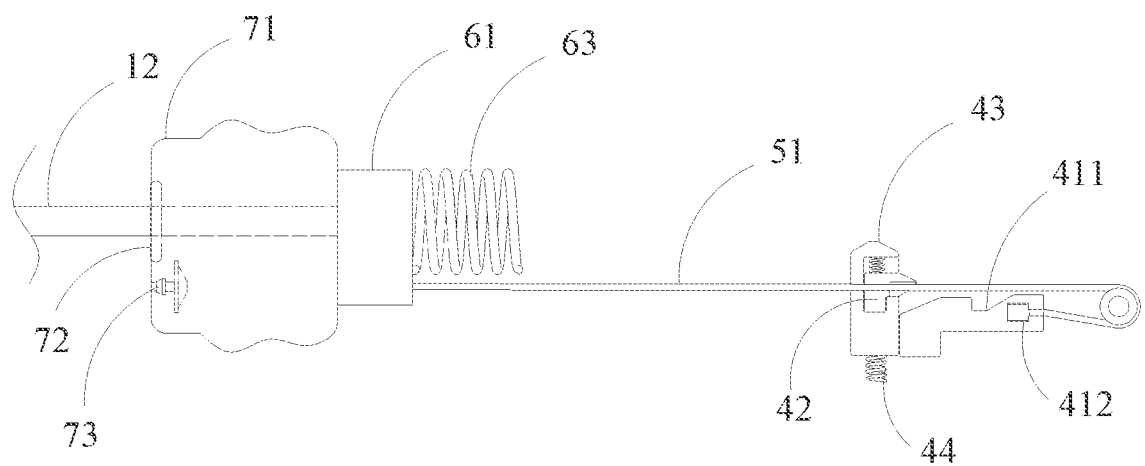
FIG. 26 is a schematic view of the closure driving mechanism in the initial state according to a seventh embodiment of the present disclosure.
Figure 27:
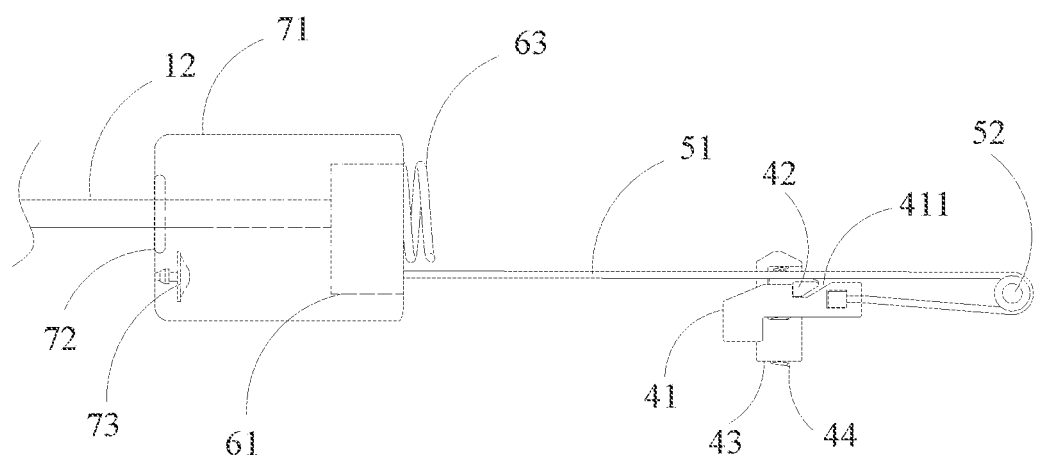
FIG. 27 is a schematic view of the closure driving mechanism after the head assembly is closed according to the seventh embodiment of the present disclosure.

FIG. 26 and FIG. 27 are schematic views of the closure driving mechanism according to a seventh embodiment of the present disclosure. The difference between this embodiment and the sixth embodiment is that, in the sixth embodiment, the driving part 61 is located inside the cylinder body 71, and the inner wall of the cylinder body 71 and the driving part 61 are enclosed to form the cavity 74; and in the seventh embodiment, the driving part 61 is located outside the cylinder body 71, and the cavity is enclosed by the inner wall of the cylinder body 71. In an alternative embodiment, part of the driving part 61 may be located inside the cylinder body 71, and part of the driving part 61 may be located outside the cylinder body 71, which all fall within the protection scope of the present disclosure.

Figure 28:
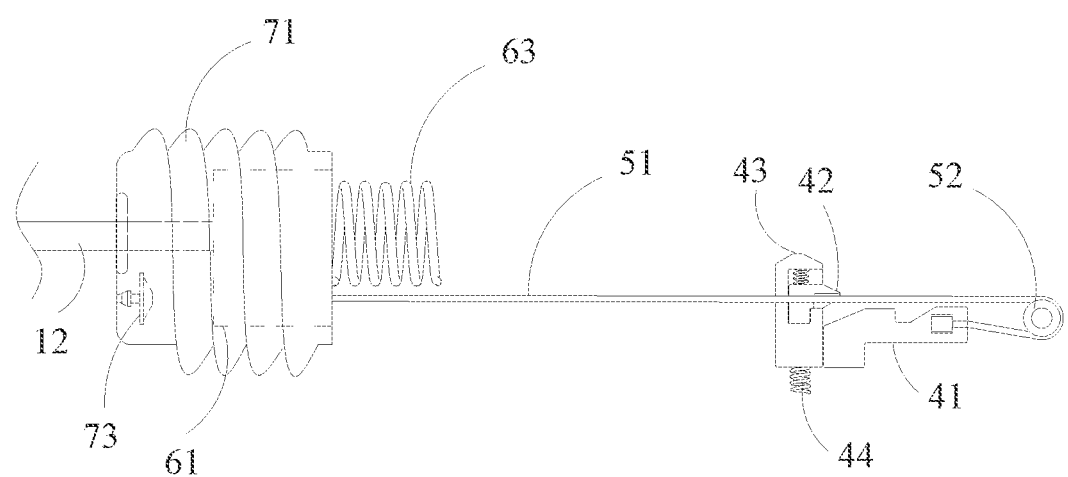
FIG. 28 is a schematic view of the closure driving mechanism according to an eighth embodiment of the present disclosure.

FIG. 28 is a schematic view of the closure driving mechanism according to an eighth embodiment of the present disclosure. The difference between this embodiment and the sixth embodiment is that, in the eighth embodiment, the cylinder body 71 is a corrugated tube extending along the axial direction of the stapler. In the initial state, the corrugated tube has an amount of compressive deformation. When the driving part 61 moves toward the proximal side of the stapler, the amount of the compressive deformation of the corrugated tube is decreased, the axial length of the corrugated tube is increased, and the volume of the cavity inside the corrugated tube is increased. When the driving part 61 moves toward the distal side of the stapler, the amount of the compressive deformation of the corrugated tube is increased, the axial length of the corrugated tube is decreased, and the volume of the cavity inside the corrugated tube is decreased.

Figure 29:
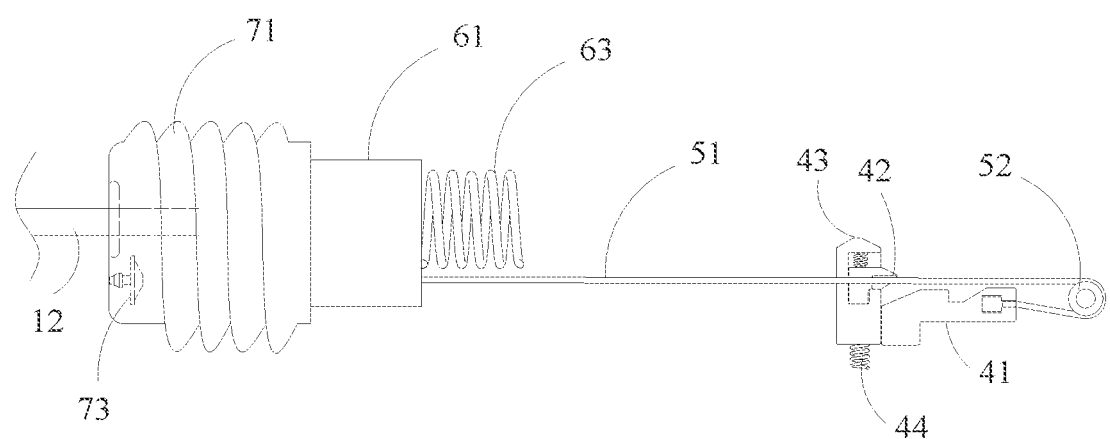
FIG. 29 is a schematic view of the closure driving mechanism according to a ninth embodiment of the present disclosure.

FIG. 29 is a schematic view of the closure driving mechanism according to a ninth embodiment of the present disclosure. The difference between this embodiment and the eighth embodiment is that, in the ninth embodiment, the driving part 61 is located outside the cylinder body 71, and the cavity is enclosed by the inner wall of the cylinder body 71.

Figure 30:
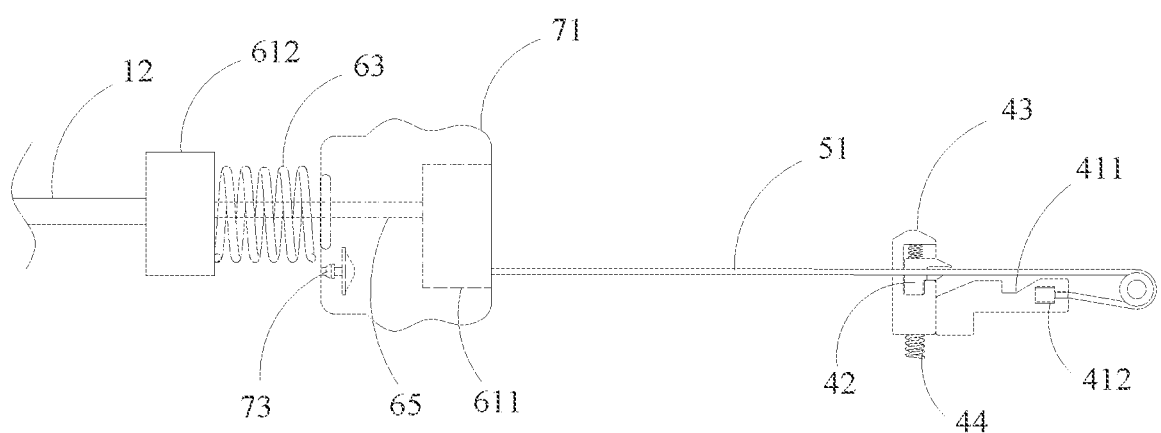
FIG. 30 is a schematic view of the closure driving mechanism according to a tenth embodiment of the present disclosure.

FIG. 30 is a schematic view of the closure driving mechanism according to a tenth embodiment of the present disclosure. The difference of this embodiment from the sixth embodiment is that, the driving part 61 includes a first driving member 611 and a second driving member 612 connected with each other, the second driving member 612 is connected with the closure pulling sheet 12, and the first driving member 611 is connected with the proximal side of the cylinder body 71. The second driving member 612 is located at the distal side of the cylinder body 71, and the second driving member 612 and the first driving member 611 are connected through a connecting rod 65. The first compression spring 63 is disposed between the proximal side of the second driving member 612 and the cylinder body 71, and can be sleeved on the connecting rod 65. When the first driving member 611 moves toward the proximal side of the stapler, the second driving member 612 is pulled to move toward the proximal side of the stapler, and the second driving member 612 compresses the first compression spring 63 to be deformed. After the pulling force toward the proximal side applied by the pulling rope 51 on the first driving member 611 is released, the second driving member 612 moves distally under the restoring force of the first compression spring 63, and drives the closure pulling sheet 12 and the first driving member 611 to move toward the distal side of the stapler. On the basis of the tenth embodiment, at least two groups of the cylinder bodies 71 and the first driving members 611 can be provided, and the second driving member 612 is fixedly connected to a plurality of the first driving members 611 at the same time, and a plurality of the one-way valves 73 are disposed in the cavities 74 of the cylinder bodies 71, respectively.

In other alternative embodiments, the first driving member 611 may be located outside the cylinder body 71, and in another alternative embodiment, the second driving member 612 may be located inside the cylinder body 71 while the compression spring 63 is disposed at the proximal side of the first driving member 611, which all fall within the protection scope of the present disclosure.

Figure 31:
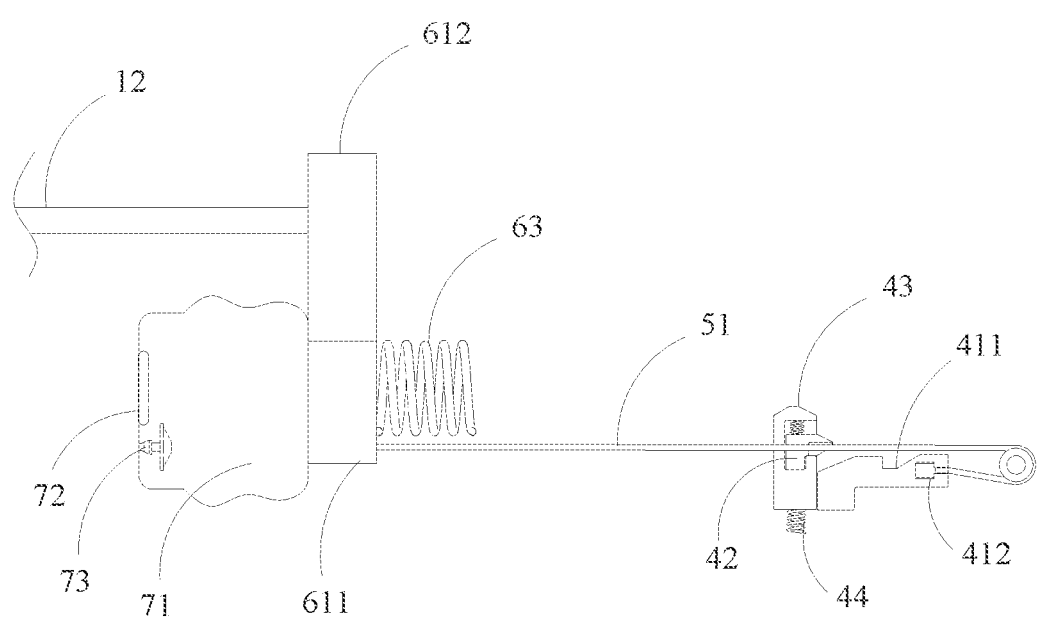
FIG. 31 is a schematic view of the closure driving mechanism according to an eleventh embodiment of the present disclosure.

FIG. 31 is a schematic view of the closure driving mechanism according to an eleventh embodiment of the present disclosure. The difference of this embodiment from the tenth embodiment is that, the closure pulling sheet 12 and the first driving member 611 are not arranged coaxially, and the second driving member 612 can be fixedly connected to a side wall of the first driving member 611. As can be seen from FIG. 31, the first driving member 611 and the second driving member 612 can be located completely outside the cylinder body 71. In this embodiment, the working principles of the second driving member 612 and the first driving member 611 are the same as those of the embodiment shown in FIG. 30, which will not be repeated here.

In each of the above embodiments, the cylinder body 71 may be a part of the housing 1 of the stapler, or may be a separate component that is fixedly connected to the housing 1 of the stapler. Structural features in the above embodiments can be combined with each other to form a new technical solution, which all fall within the protection scope of the present disclosure.

The closure driving mechanism and the medical stapler including the same provided by the present disclosure have the following advantages.

The closure driving mechanism applied on the medical stapler provided by the present disclosure includes a one-way air damping structure. When the head assembly is driven to be closed, the one-way valve is opened to communicate the cavity with outside air, and the head assembly will be driven to be closed when the driving part drives the closure pulling sheet to move toward the proximal side of the stapler. After the stapler is fired, the one-way valve is closed, the distal movement of the driving part compresses the air in the cavity, and the driving part will be slowed down by the resistance of the compressed air, so that the head assembly can be opened slowly to prevent the force of opening the jaws being too large to damage the surrounding tissues.

The above contents are further detailed descriptions of the present disclosure in conjunction with specific preferred embodiments, and it cannot be considered that the specific implementation of the present disclosure is limited to these descriptions. For those of ordinary skill in the technical field to which the present disclosure pertains, some simple deductions or substitutions can be made without departing from the concept of the present disclosure, which should be regarded as within the protection scope of the present disclosure.

What is claimed is:

1. A closure driving mechanism applied on a medical stapler, comprising a driving part and a cylinder body, wherein the driving part is connected with a closure pulling sheet of the stapler, and the driving part is located at a proximal side of the cylinder body, wherein a cavity is formed inside the cylinder body, and the cavity is provided with a one-way valve;
   when the driving part moves toward a proximal side of the stapler, a volume of the cavity is increased, the one-way valve is opened, and the driving part drives the closure pulling sheet to move proximally, so as to close a head assembly of the stapler;
   when the driving part moves toward a distal side of the stapler, the volume of the cavity is decreased, the one-way valve is closed, and the driving part drives the closure pulling sheet to move distally, so as to open the head assembly of the stapler.

2. The closure driving mechanism according to claim 1, wherein the cylinder body is a part of a housing of the stapler.

3. The closure driving mechanism according to claim 1, wherein the one-way valve is disposed on a distal side of the cylinder body.

4. The closure driving mechanism according to claim 1, wherein the cavity is further provided with an air hole communicated with air.

5. The closure driving mechanism according to claim 1, wherein the driving part is at least partially located inside the cylinder body, and an inner wall of the cylinder body and the driving part are enclosed to form the cavity.

6. The closure driving mechanism according to claim 5, wherein the driving part is movable in an axial direction of the stapler relative to the proximal side of the cylinder body.

7. The closure driving mechanism according to claim 6, wherein a first sealing member is provided between an outer wall of the driving part and the inner wall of the cylinder body.

8. The closure driving mechanism according to claim 6, wherein the driving part comprises a first driving member and a second driving member, the first driving member is at least partially located inside the cylinder body, and the second driving member is connected between the first driving member and the closure pulling sheet.

9. The closure driving mechanism according to claim 1 further comprising a sleeve tube, the cylinder body and the driving part are both sleeved on the sleeve tube, and the driving part is movable in an axial direction of the sleeve tube;
   wherein a second sealing member is provided between an outer wall of the sleeve tube and the cylinder body.

10. The closure driving mechanism according to claim 1, wherein an outer wall of the cylinder body is provided with at least one first fixing part, and a housing of the stapler is provided with a second fixing part matched with the first fixing part.

11. The closure driving mechanism according to claim 10, wherein the outer wall of the cylinder body is provided with at least one fixing slot, and the housing of the stapler is provided with a fixing beam matched with the fixing slot; or
   the outer wall of the cylinder body is provided with at least one fixing beam, and the housing of the stapler is provided with a fixing slot matched with the fixing beam.

12. The closure driving mechanism according to claim 1, wherein the driving part is connected with the proximal side of the cylinder body, when the driving part moves in an axial direction of the stapler, the proximal side of the cylinder body is driven to move in the axial direction of the stapler, and a length of the cylinder body along the axial direction of the stapler is changed.

13. The closure driving mechanism according to claim 12, wherein the driving part comprises a first driving member and a second driving member, the first driving member is connected with the proximal side of the cylinder body, and the second driving member is connected between the first driving member and the closure pulling sheet.

14. The closure driving mechanism according to claim 12, wherein a side wall of the cylinder body is a flexible side wall, the flexible side wall of the cylinder body has an amount of bending deformation in an initial state, and when the driving part moves toward the proximal side of the stapler, the amount of the bending deformation of the flexible side wall is decreased.

15. The closure driving mechanism according to claim 12, wherein a side wall of the cylinder body is an elastic side wall, when the driving part drives the proximal side of the cylinder body to move toward the proximal side of the stapler, the elastic side wall of the cylinder body is pulled and elastically deformed.

16. The closure driving mechanism according to claim 12, wherein the cylinder body is a corrugated tube extending along the axial direction of the stapler, the corrugated tube has an amount of compressive deformation in an initial state, and when the driving part moves toward the proximal side of the stapler, the amount of the compressive deformation of the corrugated tube is decreased.

17. The closure driving mechanism of claim 12, wherein a distal side of the cylinder body is fixed to a housing of the stapler.

18. The closure driving mechanism according to claim 1 further comprising a biasing member and a pulling rope, wherein the biasing member and the pulling rope are connected with the driving part, respectively;

when the head assembly of the stapler is driven to be closed, the pulling rope pulls the driving part to move toward the proximal side of the stapler, and the biasing member is deformed;

when the head assembly of the stapler is driven to be opened, the driving part moves toward the distal side of the stapler under a restoring force of the biasing member.

19. The closure driving mechanism according to claim 18 further comprising a movable handle, a slider and a turning support beam, the pulling rope is sleeved on the turning support beam, and two ends of the pulling rope are connected to the slider and the driving part, respectively;

in an initial state, when the movable handle is pressed, the movable handle drives the slider to move toward the distal side of the stapler, and the slider pulls the driving part to move toward the proximal side of the stapler through the pulling rope.

20. A medical stapler comprising the closure driving mechanism according to claim 1.

* * * * *